United States Patent [19]
McCall et al.

[11] Patent Number: 6,004,806
[45] Date of Patent: *Dec. 21, 1999

[54] OPTIMIZED MINIZYMES AND MINIRIBOZYMES AND USES THEREOF

[75] Inventors: Maxine J. McCall, Gladesville; Philip Hendry, Rozelle; Trevor Lockett, Denistone, all of Australia

[73] Assignee: Commonwealth Scientific and Industrial Research Organization, Parkville, Australia

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/488,181

[22] Filed: Jun. 7, 1995

[51] Int. Cl.$^6$ ............ C07H 21/04; C07H 21/02; C12N 15/85; C12N 15/11
[52] U.S. Cl. ............ 435/325; 435/6; 435/91.31; 435/320.1; 536/23.1; 536/23.2; 536/24.5
[58] Field of Search ............ 435/6, 91.31, 172.3, 435/240.2, 320.1, 325, 455, 375; 536/23.1, 23.2, 24.5; 514/44

[56] References Cited

U.S. PATENT DOCUMENTS

| | | | |
|---|---|---|---|
| 4,511,713 | 4/1985 | Miller et al. | 435/6 |
| 4,987,071 | 1/1991 | Cech et al. | 435/93.31 |
| 5,023,243 | 6/1991 | Tullis | 514/44 |
| 5,149,796 | 9/1992 | Rossi et al. | 536/23.2 |
| 5,298,612 | 3/1994 | Jennings et al. | 536/23.2 |

FOREIGN PATENT DOCUMENTS

| | | |
|---|---|---|
| 9051301 | 11/1990 | Australia . |
| 9062186 | 3/1991 | Australia . |
| 321201 | 2/1988 | European Pat. Off. . |
| 8804300 | 6/1988 | WIPO . |
| 9103162 | 3/1989 | WIPO . |
| 8905852 | 6/1989 | WIPO . |
| 9119789 | 12/1991 | WIPO . |

OTHER PUBLICATIONS

Cameron, F.H. et al., (1989) "Specific Gene Suppression by Engineered Ribozymes in Monkey Cells" Proc. Natl. Acad. Sci. U.S.A. 86: 9139–9143.

Cech, T.R., (1987) "The Chemistry of Self–Splicing RNA Enzymes", Science, 236: 1532–1539.

Chuat, J. et al. (1989) "Can Ribozymes Be Used To Regulate Procaryote Gene Expression?", Biochemical and Biophysical Research Communications 162: 1025–1029.

Cotten, M. et al. (1989) "Ribozyme Mediated Destruction of RNA in vivo" The EMBO Journal 8: 3861–3866.

Dahm, S.C. & Uhlenbeck, O.C. (1990) "Characterization of deoxy– and ribo–containing oligonucleotide substrates in the hammerhead self–cleavage reaction" Biochimie 72: 819–823.

Eckner, R. et al. (1991) "Mature mRNA 3' End Formation Stimulates RNA Export from the Nucleus" The EMBO Journal 10: 3513–3522.

Forster, A.C. et al., (1988) "Self–cleaving Viroid and Newt RNAs May Only Be Active As Dimers" Nature 334: 265–267.

Forster, A.C. et al., (1987) "Self–Cleaving of Virusoid Is Performed by the Proposed 55–Nucleotide Active Site" Cell 50: 9–16.

Goodchild J. & Kohli, V. (Oct. 21–24, 1990.) Ribozymes That Cleave an RNA Sequence form Human Immunodeficiency Virus. Poster No. 12 at Conference in San Diego, California on "Catalytic RNA as an anti–HIV agent: Design and Delivery to Cells".

Goodchild, J. & Kohli, V. (Feb. 1, 1991) Arch. Biochem. Biophys. 284: 386–391. "Ribozymes That Cleave an RNA sequence from Human Immunodeficiency Virus: the Effect of Flanking Sequence on Rate." Arch. Biochem. Biophys. 284: 386–391.

Hendry, P. et al., (1992) "A Ribozyme With DNA In The Hybridising Arms Display Enhance Cleavage Ability" Nucleic Acids Research 20: 5737–2741.

Haseloff, J. et al., (1989) "Sequence Required for Self–cataplysed Cleavage of the Satellite RNA of Tobacco Ringspot Virus" Gene 82:43–52.

Haseloff, J. and Gerlach, W.L., (1989) "Simple RNA Enzyme with New and Highly Specific Endoribonuclease Activities" Nature, 334: 585–591.

Huillier, A. et al., Ribozyme mediated suppression of αlactalbumin Expressed in C1271 Cells by T7/Vaccinia Virus (Abstract from conference proceedings) 51st Conference of the New Zealand Society of Animal Production, New Zealand, Feb. 11–15, 1991.

Hutchins, C.J. et al., (1986) "Self–Cleavage of Plus and Minus RNA Transcripts of Avocado Sunblotch Virus" Nucleic Acids Research, 14: 3627–3635.

Jeffries, A.C. & Symons, R.H. (Feb. 25, 1989) Nucl. Acids. Res. 17: 1371–1377. "A catalytic 13–mer."

Kikuchi, U. et al., (1991) "Site–specific cleavage of natural mRNA sequences by newly designed hairpin catalytic RNAs" Nucleic Acids Research, 19: 6751–6755.

Lamb, J.W. & Hay, R.T. (1990) "Ribozymes that Cleave Potato Leafroll Virus RNA Within the Coat Protein and Polymerase Genes", J. Gen. Virol. 71: 2257–2264.

(List continued on next page.)

*Primary Examiner*—George C. Elliott
*Assistant Examiner*—Sean McGarry
*Attorney, Agent, or Firm*—John P. White; Cooper & Dunham LLP

[57] ABSTRACT

This invention is directed to improved catalytic compounds, minizymes and miniribozymes, capable of hybridizing with a target RNA to be cleaved. The minizymes and miniribozymes and compositions of the present invention may be used in vitro or in vivo. They may be used as diagnostic or therapeutic agents.

33 Claims, 2 Drawing Sheets

OTHER PUBLICATIONS

McCall, M.J. et al. (1992) "Minimal Sequence Requirements For Ribozyme Activity" Proc. Natl. Acad. Sci. USA 89: 5710–5714.

McClain, et al., (1987) "Model Substrates for an RNA Enzyme" Science 238: 527–530.

Miller, W.A. et al., (1991) "A Satellite RNA of Barley Yellow Dwarf Virus Contains a Novel Hammerhead Structure in the Self–Cleavage Domain" Virology, 183: 711–720.

Perreault, J–P. et al., (1991) "Mixed Deoxyribo– and Ribo–Oligonucleotides with Catalytic Activity" Nature 344: 565–567.

Perreault, J–P. et al. (1991) "Relationship Between 2'–Hydroxyls and Magnesium Binding in the Hammerhead RNA Domain: a Model for Ribozyme Catalysis." Biochem. 29: 10695–10702.

Ruffner, D.E. et al., (1989) "Studies on the Hammerhead DNA Self–Cleaving Domain" Gene 82: 31–41.

Ruffner, D.E. et al., (1990) "Sequence Requirements of the Hammerhead RNA Self–Cleaving Reaction" Biochemistry 29: 10695–10702.

Sampson et al., (1987) "Characterization of Two–RNA catalyzed RNA Cleavage Reductions" Cold Spring Harbor Sym. Quant. Biol. 52: 267–275.

Sarver, N. et al. (1990) "Ribozymes as Potential Anti–HIV–1 Therapeutic Agents" Science, 247: 1222–1224.

Saxena, S. et al., (1990) "Ribozymes Correctly Cleave a Model Substrate and Endogenous RNA in vivo" J. Biol. Chem. 265:17106–17109.

Scanlon, K. et al., (1991) "Ribozyme–Mediated Cleavage of C–fos RNA Reduces Gene Expression of DNA Synthesis Enzymes and Metallothionein" Proc. Natl. Acad. Sci. USA, 88: 10591–10595.

Sheldon, C.C. & Symons, R.H., (1989) "RNA Stem Stability in the Formation of a Self–Cleaving Hammhead Structure" Nucleic Acids Research, 17: 5665–5678.

Symons, R.H. (1989) "Self–Cleavage of RNA in the Replication of Small Pathogens of Plants and Animals" Tibs 14: 445–450.

Tabler, M. & Tsagris, M., (1991) "Catalytic Antisense RNAs Produced by Incorporating ribozymes Sassettes into cDNA" Gene 108: 175–183.

Uhlenbeck et al., (1987) "A Small Catalytic Oligonucleotide" Nature 328: 596–600.

Uhlmann et al., Chemical Reviews (1990) 90: 544–584.

Weerasinghe, M. et al., (1991) "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme" Journal of Virology 65: 5531–5534.

Yang, J., Perreault, J–P., Labuda, D., Usman, N. & Cedergren, R., (Dec. 25, 1990) Biochemistry 29: 11156–11160. "Mixed DNA/RNA Polymers are Cleaved by the Hammerhead Ribozyme."

Zaug, A.J. & Cech, T.R., (1986 A) "The Interviewing Sequence RNA of Tetrahymena is an Enzyme" Science, 231: 473–474.

Zaug, A.J. et al., (1986 B) "The Tetrahymena Ribozyme Acts like and RNA Restriction Endonuclease" Nature, 234: 429–433.

Branch et al. A Good Antisense is Hard to Find. TIBS vol. 23: 45–50, Feb. 1998.

Agrawal. Antisense Oligonucleotides: Towards Clinical Trials. Tibtech vol. 14: 376–387, Oct. 1996.

Tuschl et al. Hammerhead Ribozymes: Importance of Stern–Loop II for Activity. vol. 90: 6991–6994, Aug. 1993.

Stull et al "Antigene, Ribozyme and Avtaner Nucleic Acid Drugs: Progress & Problems" *Pharmaceutical Research* vol. 12 No. 4 1995 pp. 465–483.

Shimayama et al, "Nuclease–resistant chimeric Ribozymes Containing Deoxyribonucleotides and Phosphorathionate Linkages," *Nucleic Acids Research* vol. 21, No. 11 pp. 2605–2611, 1993.

McCall et al "Minimal Sequence Requirements for Ribozyme Activity". *Proc. Natl. Acad. Sci. USA* vol. 89 pp. 5710–5714 Jul. 1992.

Barinaga, M. "Ribozymes: Killing the Messenger". *Science* vol. 262, No. 5739 p. 1512–4 1993.

CAT Expression (Mean ± SEM) for Different treatments. Each experiment is performed in triplicate.

Extent of Alamar Blue Reduction (mean ± SEM) in the same experiments as in Figure 1. Extent of reduction relates to metabolic activity of the cells during the 18 hours post-transfection.

Cleavage of IL-2 substrate (15-mer) at 37°C by minizymes (with cctt and gtttt linkers) and ribozyme with DNA arms.

OPTIMIZED MINIZYMES AND MINIRIBOZYMES AND USES THEREOF

Throughout this application various references are cited in bracket by author and publication year. The full citations are listed alphabetically and may be found immediately preceding the claims. These publications are hereby incorporated by reference into the present application.

BACKGROUND OF THE INVENTION

Several types of ribozymes have been identified in living organisms. One of the first ribozymes to show catalytic turnover was RNA of ribonuclease P. Ribonuclease P (RNase P) cleaves precursor tRNAs (pre-tRNAs) at their 5' ends to give the mature 5'-termini of tRNAs. In *Escherichia coli* and *Bacillus subtilis*, the RNase P holoenzyme is composed of one basic protein subunit of approximate $M_r$ 14,000 (119 amino acids) and one single stranded RNA molecule of 377 and 401 nucleotides, respectively [Baer, 1990; Altman 1987; Waugh, 1989; Pace, 1990; Nichols, 1988]. Another early ribozyme to show cleavage was the L-19 intervening sequence (IVS) from tetrahymena. The 413 nucleotide intervening sequence (IVS) in the nuclear rRNA precursor from *Tetrahymena thermophila* can be excised and the two exons ligated in the complete absence of any protein [Kruger, 1982; Cech, 1981]. Unique to this class of self-splicing reaction is the requirement of a guanosine or 5' guanosine nucleotide cofactor. The hammerhead self-cleavage reaction constitutes a third class of ribozymes. A number of plant pathogenic RNAs [Symons, 1989; Symons, 1990; Bruening, 1989; Bruening 1990], one animal viral RNA [Taylor, 1990] and a transcript from satellite II of DNA of the newt [Epstein, 1987; Epstein 1989] and from a Neurospora DNA plasmid [Saville, 1990] undergo a site specific self-cleavage reaction in vitro to produce cleavage fragments with a 2',3'-cyclic phosphate and a 5'-hydroxyl group. This reaction is unlike RNase P RNA cleavage of pre-tRNAs, where the internucleotide bond undergoes a phosphoryl transfer reaction in the presence of $Mg^{++}$ or other divalent cations. Metal cations may be essential to RNA catalysis [Pyle, 1993]. Other reactions documented to date show that ribozymes can catalyze the cleavage of DNA [Robertson, 1990; Herschlag 1990], the replication of RNA strands [Green, 1992], the opening of 2'-3'-cyclic phosphate rings [Pan, 1992], as well as react with phosphate monoesters [Zaug, 1986] and carbon centers [Noller, 1992; Piccirilli, 1992]. Finally, ribozymes with new kinds of catalytic reactivity are being created through techniques of in vitro selection and evolution [Breaker and Joyce, 1994; Szostak, 1992].

The ability to design a ribozyme to specifically target and cleave any designated RNA sequence has led to much interest in the potential application of hammerhead ribozymes in transgenic plants and in animal health as gene therapy agents or drugs. To improve the ability to treat a disease or target a specific nucleic acid, it is desirable to optimize the ribozyme to achieve the maximum chemical activity. While much success has been achieved in vitro in targeting and cleaving a number of designated RNA sequences (Saxena and Ackerman, 1990; Lamb and Hayes, 1991; Evans, et al., 1992; Mazzolini, et al., 1992; Homann, et al., 1993), there are fewer whole cell examples.

Previous reports have demonstrated that high levels of ribozyme expression are required to achieve reduced accumulation of target sequence in vivo [Cameron and Jennings, 1989; Cotten and Birnsteil, 1989; Sioud and Drilca, 1991; L'Huillier, et al., 1992; Perriman et al., 1993]. Additionally, a recent article suggests a necessity for the target and ribozyme to be sequestered in the same cellular compartment [Sullenger and Cech, 1993]. These reports demonstrate that hammerhead ribozymes are clearly capable of specific cleavage of a designated target RNA within a biological system.

SUMMARY OF THE INVENTION

This invention is directed to improved catalytic compounds, minizymes and miniribozymes, capable of hybridizing with a target RNA to be cleaved. The minizymes and miniribozymes and compositions of the present invention may be used in vitro or in vivo. They may be used as diagnostic or therapeutic agents.

DETAILED DESCRIPTION OF THE INVENTION

Figure 1:
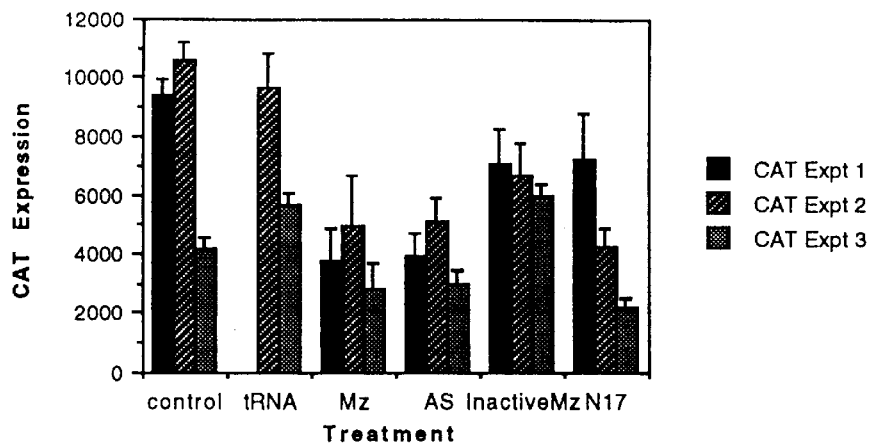
FIG. 1 shows the CAT Expression (Mean±SEM (Standard Error of the Mean)) for Different treatments. Each experiment is performed in triplicate.

This invention is directed to a compound having the formula: (Seq ID No. 1)

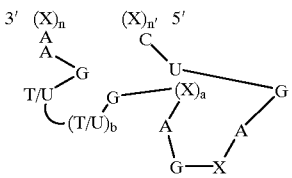

wherein each X represents a nucleotide which may be the same or different and may be substituted or modified in its sugar, base or phosphate; wherein each of $(X)_n$ and $(X)_{n'}$ represents an oligonucleotide having a predetermined sequence which is capable of hybridizing with an RNA target sequence to be cleaved; wherein each of n and n' represents an integer which defines the number of nucleotides in the oligonucleotide; wherein each solid line represents a chemical linkage providing covalent bonds between the nucleotides located on either side thereof; wherein a represents an integer which defines a number of nucleotides with the proviso that a may be 0 or 1 and if 0, the A located 5' of $(X)_a$ is bonded to the G located 3' of $(X)_a$; and wherein $(T/U)_b$ represents an oligonucleotide with the proviso that b represents an integer which is 3 or 4.

Alternatively, the compound may have the formula: (Seq ID No. 2)

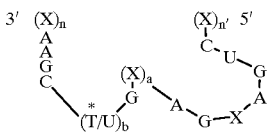

In the compounds above, the oligonucleotide 3'-(X)$_n$- is 3'-(X)$_{n-1}$-A- or may be 3'-(X)$_n$- is 3'-(X)$_{n-2}$-C-A-. Preferably, (X)$_a$ is absent. The integer b of (T/U)$_b$ is preferably equal to 3 or 4. Preferably, (T/U)$_b$ is a (T)$_b$.

The invention is also directed to compositions comprising the compound above in association with an acceptable carrier, the carrier is preferable a pharmaceutically acceptable carrier.

The invention is also directed to an oligonucleotide transfer vector containing a nucleotide sequence which on transcription gives rise to the compound above. The transfer vector may be a bacterial plasmid, a bacteriophage DNA, a cosmid, an eukaryotic viral DNA, a plant DNA virus, a geminivirus or an infective phage particle. The packaged oligonucleotide transfer vector may contain promoter sequences for RNA polymerase II, human tRNA$^{val}$ promoter or RNA polymerase III. The invention also includes a host cell transformed by the transfer vector. The host cell is a prokaryotic host cell, an eukaryotic host cell, an *E. coli* host cell, a monkey COS host cell, a Chinese hamster ovary host cell, a mammalian host cell, a plant host cell, a plant protoplast host cell, a hematopoietic host cell, a stem cell, a hematopoietic progenitor cell, a lymphoid cell, T-cell, a B-cell, pre-B cell, a CD4+T-cell or a peripheral blood mononuclear cell.

The invention also provides a method of cleaving a target mRNA in a subject which comprises administering to the subject an effective amount of the compound above or a vector capable of expressing the compound. The administration may be topical in an amount is between 1 ng and 10 mg. The administration may also be systemic and administered in an amount between 1 ng and 500 μg/kg weight/day. The administration may also be aerosol administration. A method of cleaving a target mRNA in a host cell which comprises administering to the host cell an effective amount of the compound above.

The compound above may further comprise an antisense nucleic acid which is capable of hybridizing with an RNA target sequence. The compound above may further comprise at least one additional non-naturally occurring oligonucleotide compound which comprises nucleotides whose sequence defines a conserved catalytic region and nucleotides whose sequence is capable of hybridizing with a predetermined target sequence. The compound of claim 29 wherein the additional non-naturally occurring oligonucleotide compound is a hammerhead ribozyme, a minizyme, a hairpin ribozyme, a hepatitis delta ribozyme, an RNAase P ribozyme or a combination thereof. See for example hammerhead ribozyme Haseloff et al. U.S. Pat. No. 5,254,678, issued Oct. 18, 1993; Jennings U.S. Pat. No. 5,298,612, issued Mar. 29, 1994; Group I introns, Cech et al. U.S. Pat. No. 4,740,463, issued Apr. 26, 1988; Altman et al. U.S. Pat. No. 5,168,053, issued Dec. 1, 1992 or PCT International Publication No WO 92/03566), hepatitis delta ribozymes (e.g. Blumenfeld et al. PCT International Application No. WO/90/05157) and hairpin ribozymes (European Patent Application No. EP 360,257, Hampel et al. Nuc. Acids Res. (1990) 18:299–304).

Preferred cleavage sites in the target RNA have the sequence "XUX", preferably GUC, GUU, GUA, UUA and UUC. By way of example, suitable reaction conditions may comprise a temperature from about 4 degree(s) C. to about 60 degree(s) C., preferably from about 10 degree(s) to 45 degree(s) C., more preferably from about 20 degree(s) to 43 degree(s) C., pH from about 6.0 to about 9.0 and concentration of divalent cation (such as Mg$^{2+}$) from about 1 to about 100 mM (preferably 1 to 20 mM). The nucleotides of the sequences (X)$_n$ and (X)$_{n'}$ of the compounds above may be of any number and sequence sufficient to enable hybridization with the nucleotides in the target RNA, as described herein. Ribozymes containing a small number of nucleotides in each of the groups (X)$_n$ and (X)$_{n'}$ of the compounds above (such as four nucleotides) would generally be incubated at lower temperatures, such as about 20 degree(s) C. to about 25 degree(s) C. to aid hybridizing with the nucleotide sequences in the substrate. For use in a human therapeutic, the number of nucleotides n and n' in (X)$_n$ and (X)$_{n'}$ are not necessarily equal. The invention is also directed to covalently-linked multiple ribozymes, where each ribozyme is directed to a target sequence which may be the same or different. In addition these compounds may be covalently attached to an antisense molecule which may be 10 to 100 bases in length. Antisense sequences capable of hybridizing to an RNA in a mammal or plant are well known see (Shewmaker et al. U.S. Pat. No. 5,107,065, issued Apr. 21, 1992). As the ribozyme acts as an enzyme, showing turnover, the ratio of ribozyme to substrate may vary widely.

A target RNA containing a suitable cleavage site such as XUX site may be incubated with a compound described above. The nucleotide sequences (X)$_n$ and (X)$_{n'}$ of the compounds above are selected to hybridize with their substrate. They may be selected so as to be complementary to nucleotide sequences flanking the cleavage site in the target RNA. On incubation of the ribozyme or ribozyme composition and its substrate, an enzyme/substrate complex is formed as a result of base pairing between corresponding nucleotides in the ribozyme and the substrate. Nucleotide sequences complementary to (X)$_n$ and (X)$_{n'}$ of the compounds above flanking the cleavage site in the substrate may form a double stranded duplex with (X)$_n$ and (X)$_{n'}$ as a result of base pairing, which base pairing is well known in the art [See for example: Sambrook, 1989]. The formation of a double stranded duplex between the nucleotides may be referred to as hybridization [Sambrook, 1989]. The extent of hybridization or duplex formation between the ribozyme and its substrate can be readily assessed, for example, by labelling one or both components, such as with a radiolabel, and then subjecting the reaction mixture to polyacrylamide gel electrophoresis under non-denaturing conditions [Sambrook, 1989]. If the target is cleaved specifically on incubation with the compound, the compound is active and falls within the scope of this invention. Accordingly, a ribozyme containing substituted or modified nucleotides in the conserved region may be simply tested for endonuclease activity in a routine manner.

As will be readily appreciated by workers in the field to which this invention relates, the cleavage of a target RNA may be readily assessed by various methods well known in the art [See for example: Sambrook, 1989]. Cleavage may, for example, be assessed by running the reaction products (where the substrate is radioactively labelled) on acrylamide, agarose, or other gel systems, and then subjecting the gel to autoradiography or other analytical technique to detect cleavage fragments [Sambrook, 1989].

In another embodiment, the invention provides a composition which comprises the compounds above in association with an acceptable carrier. The invention is also directed to an oligonucleotide transfer vector containing a nucleotide sequence or sequences which on transcription gives rise to the compounds above.

The transfer vector may be a bacterial plasmid, a recombinant bacterial plasmid, a bacteriophage DNA, a cosmid, or an eukaryotic viral DNA. The transfer vector may also contain a promoter sequence such as that for RNA polymerase II, RNA polymerase III, a viral promoter such as SV40 or HIV LTR, a plant promoter such as CaMV S35 or a promoter associated with animal health. Preferably, the plant or animal promoter is capable of expression in a regulated manner. Such promoter control regions would be regulated by endogenous signals to direct either tissue specific or temporal expression or by externally administered compounds to elicit transcription of downstream sequences.

The invention also provides a host cell transformed by the transfer vector as mentioned above, which may be a prokaryotic host cell or an eukaryotic host cell e.g. yeast cell or yeast protoplast, E. coli host cell, a monkey host cell (e.g. COS), a Chinese hamster ovary host cell, a mammalian host cell, a plant host cell, or a plant protoplast host cell.

In one embodiment, there is provided a packaged oligonucleotide transfer vector, as mentioned hereinabove, which is a plant virus, a mammalian virus, a geminivirus, a Ti or Ri plasmid or an infective phage particle.

In another embodiment, the composition, as discussed above, is in association with an acceptable carrier. This invention also provides a composition as discussed hereinabove wherein the oligonucleotide is an oligoribonucleotide or an RNA-DNA hybrid molecule comprising nucleotides which may be substituted or modified in their sugar, base or phosphate group. It is preferred that the oligonucleotide be an oligoribonucleotide or a hybrid RNA-DNA molecule. However, other substitutions or modifications in the nucleotide are possible providing that endonuclease activity is not lost. Such derivatives or modifications are described below.

The nucleotides may be in the form of deoxyribonucleotides, ribonucleotides, deoxyribonucleotide ribonucleotide hybrids, or derivatives thereof as herein described. The flanking sequences $(X)_n$ and $(X)_{n'}$ may be chosen to optimize stability of the ribozyme from degradation. For example, deoxyribonucleotides are resistant to the action of ribonucleases. Modified bases, sugars or phosphate linkages of nucleotides, such as phosphoramidate, or phosphorothioate linkages in the sugar phosphate chain of $X_n$ and $X_{n'}$, may also provide resistance to nuclease attack. Binding affinity may also be optimized in particular circumstances, by providing nucleotides solely in the form of ribonucleotides, deoxyribonucleotides, or combinations thereof. In some circumstances it may be necessary to optimize the composition of the sequences $(X)_n$ and $(X)_{n'}$, to maximize target RNA cleavage. The cleavage activity of ribozymes having flanking nucleotide sequences which hybridize to target sequences and which are comprised wholly of deoxyribonucleotides may, in some circumstances, have reduced activity. In such circumstances optimization may involve providing a mixture of deoxyribonucleotides and ribonucleotides in the nucleotide sequences $(X)_n$ and $(X)_{n'}$. For example, nucleotides in the ribozyme which are proximal to the cleavage site in a target RNA may be in the form of ribonucleotides.

The respective 3' and 5' termini of the sequences $(X)_n$ and $(X)_{n'}$ or alternatively the 3' and 5' end termini of the ribozyme, may be modified to stabilize the ribozyme from degradation. For example, blocking groups may be added to prevent terminal nuclease attack, in particular 3'-5' progressive exonuclease activity. By way of example, blocking groups may be selected from substituted or unsubstituted alkyl, substituted or unsubstituted phenyl, substituted or unsubstituted alkanoyl. Substituents may be selected from $C_1$–$C_5$ alkyl; halogens such as F, Cl or Br; hydroxy; amino; $C_1$–$C_5$ alkoxy and the like. Alternatively, nucleotide analogues such as phosphorothioates, methylphosphonates or phosphoramidates or nucleoside derivatives (such as alpha -anomers of the ribose moiety) which are resistant to nuclease attack may be employed as terminal blocking groups. The blocking group may be an inverted linkage such as a 3' 3' thymidine linkage or a 5' 5' pyrophosphate linkage as in the guanosine cap.

Alternatively, groups which alter the susceptibility of the ribozyme molecule to other nucleases may be inserted into the 3' and/or 5' end of the ribozyme. For example, 9-aminoacridine attached to the ribozyme may act as a terminal blocking group to generate resistance to nuclease attack on the ribozyme molecules and/or as an intercalating agent to aid endonucleolytic activity. It will be readily appreciated that a variety of other chemical groups, e.g. spermine or spermidine could be used in a related manner.

It is also possible to stabilize the ribozyme from degradation by embedding it in an RNA molecule. These molecules can be produced either in vitro or in vivo by DNA coding sequences being operably linked to transcriptional control sequences as appropriate. Examples of RNA molecules into which ribozymes could be inserted may include, but are not limited to, tRNA, mRNA, rRNA, snRNA or other RNA molecules. In addition, the ribozyme may be inserted into an engineered stable stem loop structure. The compound may also be coupled with other stabilizing structures such as a transcription terminator on the 3' end such as the T7 terminator, ρ-independent terminator, cry element (Gelfand et al. U.S. Pat. No. 4,666,848, issued May 19, 1987) or the TrpE terminator. Furthermore, sequences such as the poly (A) addition signal AATAAA may be added and strategies involving changing the length of the 3' non-coding region (see Gillies, U.S. Pat. No. 5,149,635, issued Sep. 22, 1992). Further, it is possible to insert the compound into a DNA molecule as well.

The compounds of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the ribozymes of the present invention may be associated with RNA binding peptides or proteins which may assist in bringing the ribozyme into juxtaposition with a target nucleic acid such that hybridization and cleavage of the target sequence may take place. Nucleotide sequences may be added to the respective 3' and 5' termini of the sequences $(X)_n$ and $(X)_{n'}$ or alternatively the 3' and 5' end termini of the ribozyme to increase affinity for substrates. Such additional nucleotide sequences may form triple helices with target sequences [Strobel, 1991] which may enable interaction with an intramolecularly folded substrate. Alternatively, modified bases (non-natural or modified bases as described in Principles of Nucleic Acid Structure [Saenger, 1984]) within the additional nucleotide sequences may be used that will associate with either single stranded or duplex DNA generating base pair, triplet, or quadruplet, interactions with nucleotides in the substrate. Suitable bases would include inosine, 5'-methylcytosine, 5'-bromouracil and other such bases as are well known in the art, as described, for example, in Principles of Nucleic Acid Structure [Saenger, 1984].

The compounds of this invention may be produced by nucleotide synthetic techniques which are known in the art, and described for example by Carruthers et al., Foehler et al. and Sproat et al. [Carruthers, 1987; Foehler, 1986; Sproat, 1984]. Generally, such synthetic procedures involve the sequential coupling of activated and protected nucleotide bases to give a protected nucleotide chain, whereafter protecting groups may be removed by suitable treatment. Preferably the compounds will be synthesized on an automated synthesizer such as those made by Applied Biosystems (a Division of Perkin Elmer), Pharmacia or Millipore. Alternatively, the ribozymes in accordance with this invention may be produced by transcription of nucleotide sequences encoding said ribozymes in host-cells or in cell free systems utilizing enzymes such as T3, SP6 or T7 RNA-polymerase. Further means for producing the ribozymes of this invention are further discussed below [Sambrook, 1989].

Nucleotides represented in the compounds above comprise a sugar, base, and a monophosphate group or a phosphodiester linkage. Accordingly, nucleotide derivatives or modifications may be made at the level of the sugar, base, monophosphate groupings or phosphodiester linkages. It is preferred that the nucleotides in the compounds above be ribonucleotides or RNA/DNA hybrids, however, other substitutions or modifications in the nucleotide are possible providing that endonuclease activity is not lost. More specifically, it is preferred that the catalytic region be comprised of ribonucleotides.

In one aspect of this invention, the sugar of the nucleotide may be a ribose or a deoxyribose such that the nucleotide is either a ribonucleotide or a deoxyribonucleotide, respectively. Furthermore, the sugar moiety of the nucleotide may be modified according to well known methods in the art [See for example: Saenger, 1984; Sober, 1970]. This invention embraces various modifications to the sugar moiety of nucleotides as long as such modifications do not abolish cleavage activity of the ribozyme. Examples of modified sugars include replacement of secondary hydroxyl groups with halogen, amino or azido groups; 2'-alkylation; conformational variants such as the O2'-hydroxyl being cis-oriented to the glycosyl $C_1'$ -N link to provide arabinonucleosides, and conformational isomers at carbon $C_1'$ to give alpha -nucleosides, and the like. In addition, the invention is directed to compounds with a substituted 2' hydroxyl such as 2' O-allyl, or 2' O-methyl. Alternatively, the carbon backbone of the sugar may be substituted such as in 2' C-allyl.

Accordingly, the base of the nucleotide may be adenine, guanine, cytosine, methyl cytosine, uracil, thymine xanthine, hypoxanthine, inosine, or other methylated bases.

Nucleotide bases, deoxynucleotide bases, and ribonucleotide bases are well known in the art and are described, for example in Principles of Nucleic Acid Structure [Saenger, 1984]. Furthermore, nucleotide, ribonucleotide, and deoxyribonucleotide derivatives, substitutions and/or modifications are well known in the art [See for example: Saenger, 1984; Sober, 1970], and may be made with the proviso that endonuclease activity of the ribozyme is not lost. As mentioned previously, endoribonuclease activity may be readily and routinely assessed.

In addition, a large number of modified bases are found in nature, and a wide range of modified bases have been synthetically produced [See for example: Saenger, 1984; Sober, 1970]. For example, amino groups and ring nitrogens may be alkylated, such as alkylation of ring nitrogen atoms or carbon atoms such as $N_1$ and $N_7$ of guanine and $C_5$ of cytosine; substitution of keto by thioketo groups; saturation of carbon-carbon double bonds, and introduction of a C-glycosyl link in pseudouridine. Examples of thioketo derivatives are 6-mercaptopurine and 6-mercaptoguanine. Bases may be substituted with various groups, such as halogen, hydroxy, amine, alkyl, azido, nitro, phenyl and the like. The phosphate moiety of nucleotides or the phosphodiester linkages of oligonucleotides are also subject to derivatization or modifications, which are well known in the art. For example, replacement of oxygen with nitrogen, sulphur or carbon derivatives to respectively give phosphoramidates, phosphorothioates, phosphorodithioates and phosphonates. Substitutions of oxygen with nitrogen, sulphur or carbon derivatives may be made in bridging or non bridging positions. It has been well established from work involving antisense oligonucleotides [Uhlmann, 1990] that phosphodiester and phosphorothioate derivatives may efficiently enter cells (particularly when of short length), possibly due to association with a cellular receptor. Methylphosphonates are probably readily taken up by cells by virtue of their electrical neutrality.

A further aspect of the invention provides alternative linkages such as an amide, a sulfonamide, a hydroxylamine, a formacetal, a 3'-thioformacetal, a sulfide, or an ethylene glycol function to replace the conventional phosphodiester linkage. These modifications may increase resistance towards cellular nucleases and/or improved pharmacokinetics.

Any combination of the above listed nucleotide modifications, substitutions, or derivatizations, made at the level of the sugar, base, or monophosphate groupings or phosphophodiester linkages may be made in the compounds provided that endonuclease activity is not lost.

The compounds of this invention may be incorporated and expressed in cells as a part of a DNA or RNA transfer vector, or a combination thereof, for the maintenance, replication and transcription of the ribozyme sequences of this invention.

Nucleotide sequences encoding the compounds of this invention may be integrated into the genome of a eukaryotic or prokaryotic host cell for subsequent expression (for example as described [Sambrook, 1989]). Genomic integration may be facilitated by transfer vectors which integrate into the host genome. Such vectors may include nucleotide sequences, for example of viral or regulatory origin, which facilitate genomic integration. Methods for the insertion of nucleotide sequences into a host genome are described for example in Sambrook et al. and Hogan et al. [Sambrook, 1989; Hogan, 1986; 1989].

Nucleic acid sequences encoding the ribozymes of this invention integrated into the genome may preferably include promoter and enhancer elements operably linked to the nucleotide sequence encoding the ribozyme of this invention, and capable of expressing said ribozyme in a eukaryotic (such as animal or plant cells) or prokaryotic (such as bacteria) host cells. Ideally, the promoter and enhancer elements are designed for expression in a tissue and/or developmentally specific manner.

Additionally, the compounds of the present invention may be prepared by methods known per se in the art for the synthesis of RNA molecules. (For example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T3 or T7 polymerase or SP6 RNA polymerase. A DNA sequence corresponding to a ribozyme of the present invention may be ligated into a DNA transfer vector, such as plasmid or bacteriophage DNA. Where the transfer vector contains an RNA polymerase promoter operably linked to DNA corresponding to a ribozyme, the ribozyme may be conveniently produced upon incubation with an RNA polymerase. Ribozymes may, therefore, be produced in vitro by incubation of RNA polymerase with an RNA polymerase promoter operably linked to DNA corresponding to a ribozyme, in the presence of ribonucleotides. In vivo, prokaryotic or eukaryotic cells (including mammalian, plant and yeast cells) may be transfected with an appropriate transfer vector containing genetic material corresponding to a ribozyme in accordance with the present invention, operably linked to an RNA polymerase promoter such that the ribozyme is transcribed in the host cell. Transfer vectors may be bacterial plasmids or viral (RNA and DNA). Nucleotide sequences corresponding to ribozymes are generally placed under the control of strong promoters such as, the lac, SV40 late, SV40 early, metallothionein, or lambda promoters. Particularly useful are promoters regulated in a tissue or a temporal (developmental) specific manner. The vector may be an adenovirus or an adeno-associated virus. See for example PCT International Publication No. WO 93/03769, "Adenovirus Mediated Transfer of Genes to the Gastrointestinal Tract", U.S. Ser. No. 747,371; PCT International Publication No. WO 94/11506, "Adenovirus-Mediated Gene Transfer to Cardiac and Vascular Smooth Muscle," J. Leiden et al., U.S. Ser. No. 07/977,496; PCT International Publication No. WO 94/11522, "Vector for the Expression of Therapy-Relevant Genes," U. Stein et al., PCT International Publication No. WO 94/11524, "Targetable Vector Particles," W. Anderson et al., U.S. Ser. No. 973,307; PCT International Publication No. WO 94/17832, "Targeting and Delivery of Genes and Antiviral Agents into Cells by the Adenovirus Penton," G. Nemerow et al., U.S. Ser. Nos. 08/046,159 and 08/015,225. Ribozymes may be directly transcribed in vivo from a transfer vector, or alternatively, may be transcribed as part of a larger RNA molecule. For example, DNA corresponding to ribozyme sequences may be ligated into the 3' end of a reporter gene, for example, after a translation stop signal. Larger RNA molecules may help to stabilize the ribozyme molecules against nuclease digestion within cells. On translation the reporter gene may give rise to a protein, possibly an enzyme whose presence can be directly assayed.

The compounds of this invention may be involved in gene therapy techniques, where, for example, cells from a human suffering from a disease, such as HIV, are removed from a patient, treated with the ribozyme to inactivate the infectious agent, and then returned to the patient to repopulate a target site with resistant cells, so called ex vivo therapy. In the case of HIV, nucleotide sequences encoding ribozymes of this invention capable of inactivating the HIV virus may be integrated into the genome of lymphocytes or may be expressed by a non-integrating vector such as adenovirus. Such cells would be resistant to HIV infection and the progeny thereof would also confer such resistance.

A transfer vector such as a bacterial plasmid or viral RNA or DNA, encoding one or more of the compounds, may be transfected into cells of an organism in vivo [See for example: Llewellyn, 1987; Hanahan, 1983]. Once inside the cell, the transfer vector in some cases may replicate and be transcribed by cellular polymerases to produce ribozyme RNAs which may have ribozyme sequences of this invention; the ribozyme RNAs produced may then inactivate a desired target RNA. Alternatively, a transfer vector containing one or more ribozyme sequences may be transfected into cells by electroporation, PEG, high velocity particle bombardment or lipofectants, or introduced into cells by way of micromanipulation techniques such as microinjection, such that the transfer vector or a part thereof becomes integrated into the genome of the host cell. Transcription of the integrated genetic material gives rise to ribozymes, which act to inactivate a desired target RNA.

Transfer vectors expressing ribozymes of this invention may be capable of replication in a host cell for stable expression of ribozyme sequences. Alternatively, transfer vectors encoding ribozyme sequences of this invention may be incapable of replication in host cells, and thus may result in transient expression of ribozyme sequences. Methods for the production of DNA and RNA transfer vectors, such as plasmids and viral constructs are well known in the art and are described for example by Sambrook et al. [Sambrook, 1989].

Transfer vectors would generally comprise the nucleotide sequence encoding the ribozyme of this invention, operably linked to a promoter and other regulatory sequences required for expression and optionally replication in prokaryotic and/or eukaryotic cells. Suitable promoters and regulatory sequences for transfer vector maintenance and expression in plant, animal, bacterial, and other cell types are well known in the art and are described for example in Hogan [Hogan, 1986; 1989].

The ribozymes of the present invention have extensive therapeutic and biological applications. For example, disease causing viruses in man and animals may be inactivated by administering to a subject infected with a virus, a ribozyme in accordance with the present invention adapted to hybridize to and cleave RNA transcripts of the virus. Such ribozymes may be delivered by parenteral or other means of administration. Alternatively, a subject infected with a disease causing virus may be administered a non-virulent virus such as vaccinia or adenovirus which has been genetically engineered to contain DNA corresponding to a ribozyme operably linked to an RNA promoter, such that the ribozyme is transcribed in the cells of the host animal, transfected with the engineered virus, to effect cleavage and/or inactivation of the target RNA transcript of the disease causing virus.

The ribozymes of the present invention have particular application to viral diseases caused for example, by the herpes simplex virus (HSV) or the AIDS virus (HIV). Further examples of human and animal disease which may be treated with the ribozymes of this invention include psoriasis, cervical preneoplasia, papilloma disease, bacterial and prokaryotic infection, viral infection and neoplastic conditions associated with the production of aberrant RNAs such as occurs in chronic myeloid leukemia. Diseases or infections which may be treated in plants with ribozymes of this invention include fungal infection, bacterial infections (such as Crown-Gall disease) and disease associated with plant viral infection. Of particular interest would be compounds targeting genes associated with male gametophyte development. Examples include PCT International Publication No. WO 92/18625, entitled "Male-Sterile Plants, Method For Obtaining Male-Sterile Plants And Recombinant DNA For Use Therein"; U.S. Pat. No. 5,254,802, entitled "Male Sterile Brassica Plants," S. Hoekstra et al.; PCT International Publication No. WO 93/25695, entitled "Maintenance of Male-Sterile Plants," M. Williams et al., claiming the priority of U.S. Ser. Nos. 07/970,840 and 07/899,072; PCT International Publication No. WO 94/25593, entitled "Method For Obtaining Male-Sterile Plants" Stiekema et al.; PCT International Publication No. WO 94/29465, entitled "Process For Generating Male Sterile Plants" Dirks et al.

The period of treatment would depend on the particular disease being treated and could be readily determined by a physician or by a plant biologist as appropriate. Generally treatment would continue until the disease being treated was ameliorated.

The ribozymes of the present invention also have particular application to the inactivation of RNA transcripts in bacteria and other prokaryotic cells, plants, animals and yeast cells. In bacteria, RNA transcripts of, for example, bacteriophage, (which cause bacterial cell death) may be inactivated by transfecting a cell with a DNA transfer vector which is capable of producing a ribozyme in accordance with the present invention which inactivates the phage RNA. Alternatively, the ribozyme itself may be added to and taken up by the bacterial cell to effect cleavage of the phage RNA. Similarly, eukaryotic and prokaryotic cells in culture may, for example, be protected from infection or disease associated with mycoplasma infection, phage infection, fungal infection and the like.

RNA transcripts in plants may be inactivated using ribozymes encoded by a transfer vector such as the Ti plasmid of *Agrobacterium tumefaciens*. When such vectors are transfected into a plant cell and integrated, the ribozymes are produced under the action of RNA polymerase and may effect cleavage of a specific target RNA sequence. Endogenous gene transcripts in plants, animals or other cell types may be inactivated using the compounds of the present invention. Accordingly, undesirable phenotypes or characteristics may be modulated. It may, for example, be possible using the ribozymes of the present invention to remove stones from fruit or treat hereditary diseases in humans which are caused by the production of a deleterious protein, or over production of a particular protein. The compounds described above may be used to effect male sterility by destroying the pollen production in a plant. Furthermore, for the in vivo applications of the ribozymes of this invention in humans, animals, plants, and eukaryotic and prokaryotic cells, such as in phenotypic modification and the treatment of disease, it is necessary to introduce the ribozyme into cells whereafter, cleavage of target RNAs takes place. In vivo applications are highly suitable to the compounds as discussed herein.

Methods for the introduction of RNA and DNA sequences into cells, and the expression of the same in prokaryotic and eukaryotic cells are well known in the art for example as discussed by Cotten and Friedman [Cotten, 1990; Friedman, 1989]. The same widely known methods may be utilized in the present invention.

The compounds of this invention may be incorporated into cells by direct cellular uptake, where the ribozymes of this invention would cross the cell membrane or cell wall from the extracellular environment. Agents may be employed to enhance cellular uptake, such as liposomes or lipophilic vehicles, cell permeability agents, such as dimethylsulfoxide, and the like.

The compounds of the present invention may be combined with pharmaceutically and veterinarally acceptable carriers and excipients which are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., Edited by Ostol et al., which is incorporated herein by reference.

Agriculturally acceptable carriers and excipients are well known in the art and include water; surfactants; detergents; particularly biodegradable detergents; talc; inorganic and/or organic nutrient solutions; mineral earths and clays; calcium carbonate; gypsum; calcium sulfate; fertilizers such as ammonium sulfate, ammonium phosphate, urea, carborundum, and *agrobacterium tumefaciens;* and natural products of vegetable origin such as, for example, grain, meals and flours, bark meals; and the like.

The compounds of this invention may be provided in a composition with one or more anti-viral, anti-fungal, anti-bacterial, anti-parasitic, anti-protozoan or antihelminthic agents, herbicides, pesticides or the like, for example as described in the Merck Index (1989) 11th Edition, Merck & Co. Inc.

By way of example only, therapeutic compositions of this invention may be directed against Herpes Simplex virus types 1 and 2, psoriasis, cervical preneoplasia, papilloma disease, and bacterial and prokaryotic infection. Such treatments may, for example, involve topical application of ribozyme to the site of disease. For example, in the treatment of Herpes virus lesions, ribozymes may be formulated into a cream containing a concentration of 0.1 nM to 100 mM ribozyme, preferably 1 nM to 1 mM. The cream may then be applied to the site of infection over a 1 to 14 day period in order to cause amelioration of symptoms of the infection. Prior to the final development of topical formulations for the treatment of virus infection, effectiveness and toxicity of the ribozymes and formulations involving them may, for example, be tested on an animal model, such as scarified mouse ear, to which virus particles, such as $2\times10^6$ plaque forming units are added. A titer of infectious virus particles in the ear after treatment can then be determined to investigate effectiveness of treatment, amount of ribozyme required and like considerations. Similar investigations in animal models prior to human trials may also be conducted, for example, in respect of the treatment of psoriasis, papilloma disease, cervical preneoplasia, and in diseases such as HIV infection, bacterial or prokaryotic infection, viral infection and various neoplastic conditions, which neoplastic conditions involve a deleterious RNA species.

Compositions for topical application are generally in the form of creams, where the ribozymes of this invention may be mixed with viscous components. The compounds of this invention may be incorporated into liposomes or other barrier type preparations to shield the ribozymes from nuclease attack or other degradative agents (such as nucleases and adverse environmental conditions such as UV light).

Compositions may be provided as unit dosages, such as capsules (for example gelatin capsules), tablets, suppositories and the like. Injectable compositions may be in the form of sterile solutions of ribozyme in saline, dextrose or other media. Compositions for oral administration may be in the form of suspensions, solutions, syrups, capsules, tablets and the like. Ribozymes may also be provided in the form of an article for sustained release, impregnated bandages, patches and the like. The compounds of this invention may be embedded in liposomes or biodegradable polymers such as polylactic acid. Pharmaceutical compositions which may be used in this invention are described, for example, in Remington's Pharmaceutical Sciences, see above.

The present invention is further directed to a plant DNA expression cassette comprising a gene sequence flanked by promoter and terminator sequences at its 5'- and 3' ends respectively wherein said genetic sequence on expression provides a ribozyme RNA. The DNA cassette may further be part of a DNA transfer vector suitable for transferring the DNA cassette into a plant cell and insertion into a plant genome. In a most preferred embodiment of the present invention, the DNA cassette is carried by broad host range plasmid and which is capable of transformation into plant cells using Agrobacterium comprising Ti DNA on the left and right borders, a selectable marker for prokaryotes, a selectable marker for eukaryotes, a bacterial origin of replication and optional plant promoters and terminators such as pGA470. The present invention also includes other means of transfer such as genetic bullets (e.g. DNA-coated tungsten particles, high-velocity micro projectile bombardment) and electroporation amongst others [Maliga, 1993; Bryant, 1992; or Shimamoto, 1989].

The present invention is also directed to a transgenic plant resistant to a virus, its genome containing a sequence which gives rise, on transcription, to the nucleic acid molecule mentioned above. This transgenic plant, including fruits, and seeds thereof, may be from alfalfa, apple, arabidopsis, barley, bean, canola (oilseed rape), cantaloupe, carnation, cassava, clover, corn, cotton, courgette, cucumber, grape, melon, papaya, pepper, potato, rice, rose, snap dragon, soybean, squash, strawberry, sunflower, sweet pepper, tobacco, tomato, walnut, wheat or zucchini. Also included are the plant cells transformed by the above-mentioned transfer vector, as well as a prokaryotic, eukaryotic or yeast, plant or animal cell, comprising a nucleotide sequence which is, or on transcription gives rise to, the nucleic acid molecule.

The present invention will now be illustrated by way of non-limiting Examples only, with reference to the following non-limiting Examples, and Figures.

Experiment 1

Minizymes containing the deoxyribonucleotides d(GTTTT) and d(GTTTTT) between the conserved nucleotides $A_9$ and $G_{12}$ offer the following advantages:
  (i) These minizymes show the fast cleavage rates in vitro. See following data for the test systems Interleukin-2, TAT, CAT, and TNFα.
  (ii) The CAT minizyme (CATMgtttt) shows activity against CAT in CHO cells (see Example 2).
  (iii) The IL2 minizyme (IL2Mgtttt) shows activity against Interleukin-2 in PBMN cells (see Experiment 3) (Seq ID No. 3).

```
Minizyme g t t t t
     3'    ...xxxxxCA          xxxxxxx......  5'
                   A           CUG
                   A               A
```

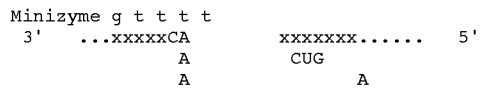

1. Method for Determining Rates of Cleavage ($k_{obs}$) by Minizymes

In these experiments, conditions are optimized so that the rate-limiting step in the reaction is cleavage of the substrate. The substrate consists of only a small number of nucleotides, in order to prevent strong self-association, and hence substrate association with the minizyme is not rate-limiting. In addition, the minizyme concentration is at least two-fold greater than substrate concentration, which is high enough to force all substrate molecules to be bound by minizyme. Thus, the measured rate in these experiments should be rate of cleavage of the substrate.

The substrate is labelled on its 5' end with [$^{32}$P]-phosphate. In general, the minizyme and substrate are heated together in buffer for two minutes at 80° C. without magnesium before putting to 37° C., in order to denature the nucleic-acid molecules; however, this step has been shown not to be necessary in a number of cases. The cleavage reaction is initiated by adding Mg$^{++}$ to the mixture at 37° C. [MgCl$_2$]=10 mM, [Tris.HCl buffer]=50 mM, [Minizyme]=5 μM (typically), [Substrate]=2 μM (typically), temperature= 37° C., pH 8.2 (for Interleukin-2 and TAT systems) and pH 8.0 (for CAT and TNFα systems). Samples are taken from the reaction mixture at various times, and the reaction is stopped by adding excess EDTA and formamide. The samples are electrophoresed on a polyacrylamide gel containing 7M urea, and the amounts of 5'-product and uncleaved substrate are quantified using a PhosphorImager (Molecular Dynamics) and ImageQuant software. Kinetic parameters are obtained by fitting the data for % of product formed ($P_t$) versus time (t) to the equation $$P_t = P_\infty - (\exp(-k_{obs}t)P_A)$$

where $P_t$ is the amount of product at time t, $P_\infty$ is the amount of product at t=$\infty$, $k_{obs}$ is the first-order rate-constant for the reaction, and $P_A$ is the difference between the percentage of product at t=$\infty$ and t=0. This is a conventional first-order kinetic equation from which $k_{obs}$, $P_\infty$, and $P_A$ are determined by least-squares fitting of the data.

2. Sequences of Molecules

Upper-case letters represent ribonucleotides, lower-case letters represent deoxyribonucleotides.

Interleukin-2 system. (Seq ID No. 4–8)
Substrate (15-mer)

5' UCCUGUC UUGCAUUg 3'

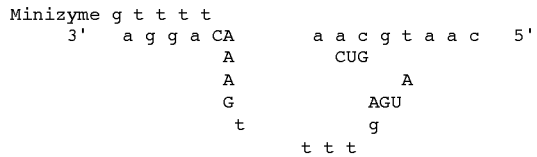

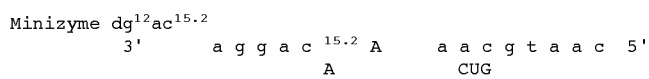

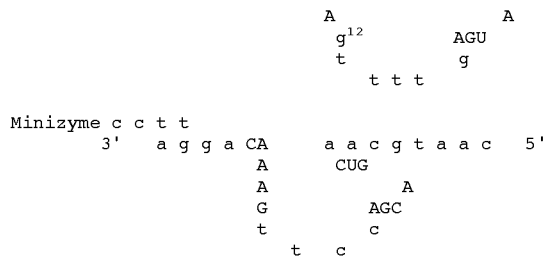
Other interleukin-2 minizymes. "x" represents the deoxyribonucleotides forming the linker between the ribonucleotides. The various sequences of "x" that have been tested appear in the following table (Table 1).
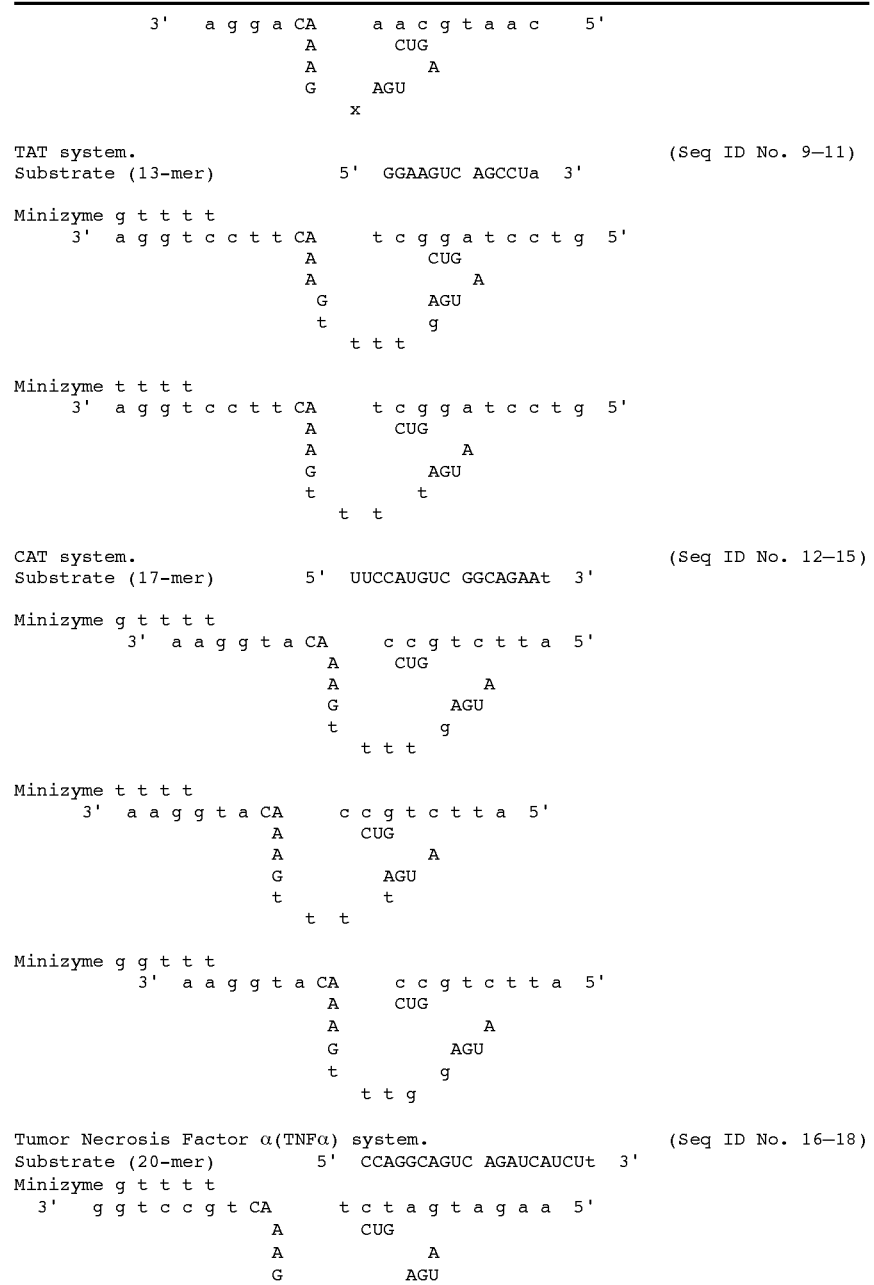

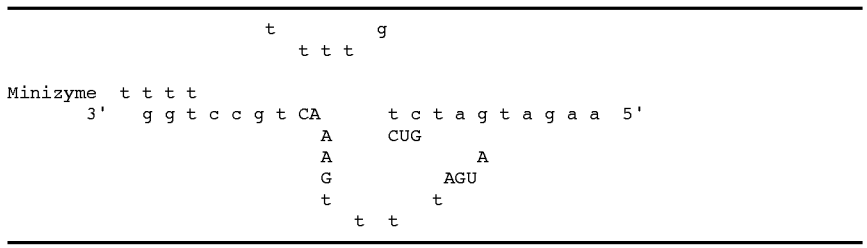

3. Observed Cleavage Rate ($k_{obs}$ min$^{-1}$) and Extent of Cleavage (% $P_\infty$) of Short Substrates by Minizymes with Various Linkers. (Table 1)

Experimental conditions: 10 mM MgCl$_2$, 50 mM Tris.HCl, pH 8.2 (for Interleukin-2 and TAT systems) and pH 8.0 (for CAT and TNFα systems), 37° C., [Substrate]=2 μM, [Minizyme]=5 μM (except [TNFM4t, TNFMg4t]=4.3 μM).

| Minizyme linker | Expt. 1 | | Expt. 2 | | Expt. 3 | | Mean | | | |
|---|---|---|---|---|---|---|---|---|---|---|
| | $k_{obs}$ | % $P_\infty$ | $k_{obs}$ | % $P_\infty$ | $k_{obs}$ | % $P_\infty$ | $k_{obs}$ | (σ) | % $P_\infty$ | (σ) |
| Interleukin-2 | | | | | | | | | | |
| 5' × 3' | | | | | | | | | | |
| cctt | 0.010 | 80# | 0.011 | 80# | | | 0.011 | (.001) | 80# | |
| tttt | | | 0.052 | 81.1 | 0.049 | 84.2 | 0.051 | (.002) | 83 | (2) |
| ttttt | | | 0.058 | 86.1 | 0.064 | 82.1 | 0.061 | (.004) | 84 | (3) |
| ttttc | 0.016 | 76.3 | 0.015 | 80.0 | | | 0.016 | (.001) | 78 | (3) |
| gttt | 0.118 | 82.3 | 0.107 | 84.5 | | | 0.113 | (.008) | 83 | (2) |
| gtttt | 0.299 | 83.5 | 0.287 | 85.3 | 0.225 | 84.9 | 0.270 | (.040) | 85 | (1) |
| gttttt | 0.287 | 82.4 | 0.253 | 84.1 | | | 0.270 | (.024) | 83 | (1) |
| gtttttt | 0.200 | 84.3 | 0.169 | 88.6 | | | 0.185 | (.022) | 86 | (3) |
| gttta | 0.026 | 85.9 | 0.022 | 94.7 | | | 0.024 | (.003) | 90 | (6) |
| gtttta | 0.047 | 81.0 | 0.038 | 88.4 | | | 0.043 | (.006) | 85 | (5) |
| gtttg | 0.122 | 82.3 | 0.092 | 89.8 | 0.107 | 83.9 | 0.107 | (.015) | 85 | (4) |
| gttttg | 0.101 | 82.1 | 0.094 | 84.2 | | | 0.098 | (.005) | 83 | (2) |
| ggttt | 0.049 | 82.4 | 0.048 | 89.4 | | | 0.049 | (.001) | 86 | (5) |
| gtgtt | 0.178 | 83.0 | 0.181 | 83.2 | | | 0.180 | (.002) | 83 | (1) |
| gttgt | 0.065 | 93.9 | 0.072 | 85.3 | | | 0.069 | (.005) | 90 | (6) |
| gtttt(dg$^{12}$dc$^{15.2}$) | 0.041 | 90.0 | 0.040 | 91.7 | | | 0.041 | (.001) | 91 | (1) |
| TAT | | | | | | | | | | |
| tttt | 0.074 | 89.1 | 0.067 | 91.9 | | | 0.071 | (.005) | 91 | (2) |
| gtttt | 0.179 | 89.7 | 0.190 | 90.8 | | | 0.185 | (.008) | 90 | (1) |
| CAT | | | | | | | | | | |
| tttt | 0.186 | 82.9 | 0.175 | 84.7 | | | 0.181 | (.008) | 84 | (1) |
| gttt^ | 0.526* | 60.8 | 0.448* | 63.8 | 0.478* | 62.8 | 0.48* | (0.04) | 62 | (2) |
| gtttt^ | 0.791* | 72.0 | 0.809* | 71.4 | | | 0.80* | (0.01) | 72 | (1) |
| gtttt^ | 0.650* | 63.0 | | | | | | | | |
| gtttt^^ | 0.453* | 61.0 | | | | | | | | |
| gtttt | | | | | | | 0.59* | (0.16) | 65 | (5) |
| ggttt | 0.278* | 68.8 | 0.352* | 67.6 | | | 0.32* | (0.05) | 68 | (1) |
| TNFα | | | | | | | | | | |
| tttt | 0.002 | 70.0# | 0.002 | 70.0# | | | 0.002 | (.001) | 70.0# | |
| gtttt | 0.274 | 59.0 | 0.180 | 74.2 | 0.303 | 58.7 | 0.25 | (0.06) | 64 | (9) | fixed at this value.
^four different syntheses, ^^average of data for the four syntheses.
*reaction is biphasic; rate constant for the initial faster reaction is given.

TABLE 2

4. Minizymes with 5'd(GTTTT) linkers have improved cleavage activity in vitro compared with those with 5'd(TTTT) linkers.

| System | $k_{obs}$ (Mgtttt) | $k_{obs}$ (Mtttt) | $k_{obs}$ (Mgtttt)/$k_{obs}$(Mtttt) |
|---|---|---|---|
| Interleukin-2 | 0.270 | 0.051 | 5.3 |
| TAT | 0.185 | 0.071 | 2.6 |
| CAT | 0.59 | 0.181 | 3.3 |
| TNFα | 0.25 | 0.002 | 125 |

The data in table 2 show that the minizymes with gtttt inkers consistently show $k_{obs}$ values of 0.2 min$^{-1}$ or better. Since we know that IL2Mgtttt, with $k_{obs}$=0.27 min$^{-1}$, is active in cells (see Example 3), we can conclude that a minizyne with at least this level of activity in an in vitro system should not be hindered in cells by its $k_{obs}$ value (i.e. rate of cleavage should not be rate limiting in cells), all other things being equal (such as target site being accessible).

Example 2

Minizyme Suppression of CAT Expression in CHO Cells

Introduction

Minizymes are sequence specific RNA endonucleases derived from standard hammerhead ribozymes by elimination of helix II. Minizymes have been shown to exhibit significant in vitro cleavage activity against both short RNA targets as well as long transcribed RNA. This report describes the testing of a particular minizyme targeted against the mRNA of CAT (Chloramphenicol acetyl transferase) expressed in a mammalian cell line. The minizyme is a chimeric DNA/RNA molecule synthesized by solid phase methods and transfected into a CHO (chinese hamster ovary) cell line stably expressing CAT.

Experimental Protocol

A CHO based CAT expressing cell line MC 11, in which CAT is expressed from the Human metallothionein IIA (MT) promoter, was used in all experiments. The MT promoter is transcriptionally active at very low metal concentration and a reasonable level of CAT expression is observed in the absence of induction by added metals.

8×10$^4$ cells were plated out in EMEM containing 10% foetal calf serum and allowed to attach overnight (14–16 hours). The cells were washed once with 1×PBS to remove serum, then the test molecules (pre-treated for 30 minutes with 1μL of lipofectamine (GIBCO BRL, Life Technologies, Maryland, USA) in serum-free EMEM) were transferred to the cells. The final concentration of test molecules was 10 μM. After four hours both serum and Alamar Blue (Alamar Bio-Sciences Inc, Sacramento Calif.) (each to a final concentration of 10%) was added to the cells and incubation continued for a further 18 hours. At this time the supernatant was removed and the cumulative cell metabolic activity determined by measuring the extent of reduction of the Alamar Blue reagent. The cells were harvested and CAT activity assayed (Sleigh, 1986).

Alamar Blue Assay

Alamar Blue is a commercial material designed for use in cytotoxicity assays for cells in culture. The reagent is reduced intracellularly in an energy dependent fashion. The reduced form of the reagent is readily quantified by either its absorption spectrum or by fluorescence. We have quantified the reduced form of Alamar Blue by absorption spectroscopy.

Target mRNA

The target site in the CAT mRNA corresponds to CAT site 3 described in Haseloff and Gerlach (1988). The cleavage triplet is a GUC site and is located towards the 3' end 662 nucleotides from the ATG start codon.

Sequences of Molecules

The test molecules are as follows: (Seq ID No. 19–22)

Lower case letters are DNA, upper case letters are RNA.

```
tRNA                 Yeast tRNA (Sigma) Phenol/Chloroform extracted.
N17                  5' nnn nnn nnn nnn nnn nn 3' (n = a, g, c or t)
CAT Antisense        5' att ctg ccg aca tgg aa 3'
CAT Minizyme         5' att ctg cc CUGAUGA gtttt GAAAC atg gaa 3'
CAT Inactive Minizyme 5' att ctg cc CUGAUGA gtttt GAGAC atg gaa 3'
```

Results

TABLE 2

Data from three Independent Experiments

| Treatment | Replicas | CAT Activity ± SEM | Alamar Blue ± SEM |
|---|---|---|---|
| Experiment 1' | | | |
| serum starved + lipofectamine | 3 | 9385 ± 318 | 1.08 ± 0.06 |
| Minizyme | 3 | 3788 ± 603 | 1.19 ± 0.06 |
| Antisense | 3 | 3885 ± 490 | 0.975 ± 0.05 |
| Inactive Minizyme | 3 | 7043 ± 695 | 1.085 ± 0.01 (n = 2) |
| N$_{17}$ | 3 | 7254 ± 876 | 0.966 ± 0.06 |
| Experiment 2' | | | |
| serum starved + lipofectamine | 2 | 10573 ± 455 | 1.045 ± 0.03 |
| tRNA | 3 | 9680 ± 656 | 0.938 ± 0.04 |
| Minizyme | 3 | 4943 ± 974 | 0.953 ± 0.02 |
| Antisense | 3 | 5073 ± 467 | 0.883 ± 0.01 |
| Inactive Minizyme | 3 | 6641 ± 642 | 0.872 ± 0.05 |
| N$_{17}$ | 3 | 4260 ± 342 | 0.857 ± 0.05 |
| Experiment 3' | | | |
| serum starved + lipofectamine | 2 | 4143 ± 269 | 0.89 ± 0.05 |
| tRNA | 3 | 5646 ± 235 | 0.781 ± 0.02 |
| Minizyme | 3 | 2855 ± 491 | 1.031 ± 0.07 |
| Antisense | 3 | 2978 ± 259 | 0.712 ± 0.10 |
| Inactive Minizyme | 3 | 5969 ± 225 | 0.778 ± 0.04 |
| N$_{17}$ | 3 | 2210 ± 195 | 0.767 ± 0.04 |

TABLE 3

Mean ± SEM CAT Expression as a percentage of Control.
(Controls are serum starved + lipofectamine treated cells)

| Treatment | Experiment 1 | Experiment 2 | Experiment 3 | Mean ± SEM |
|---|---|---|---|---|
| Control | 100 ± 13.3 | 100 ± 4.3 | 100 ± 6.5 | 100 |
| tRNA | — | 91.6 ± 6.8 | 136.3 ± 4.2 | 114 ± 22 |
| Minizyme | 49.4 ± 15.9 | 46.8 ± 19.7 | 68.9 ± 17.2 | 52 ± 9 |
| Antisense | 41.4 ± 12.6 | 48.0 ± 9.2 | 71.9 ± 8.7 | 54 ± 9 |
| Inactive Minizyme | 75.0 ± 9.9 | 62.8 ± 9.7 | 144.1 ± 3.8 | 94 ± 25 |
| $N_{17}$ | 77.3 ± 12.1 | 40.3 ± 8.0 | 53.3 ± 8.8 | 57 ± 11 |

Figure 2:
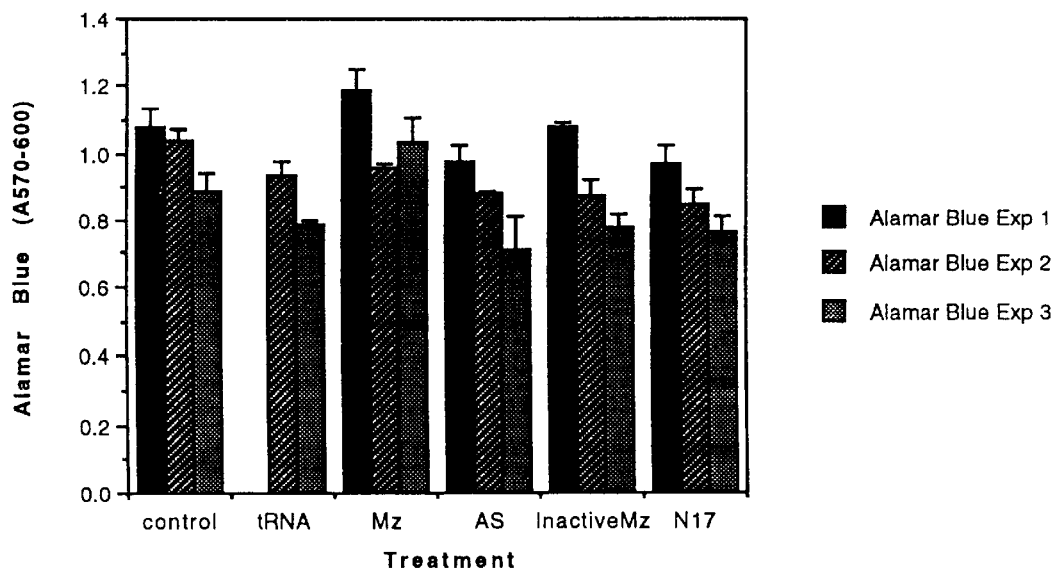
FIG. 2 shows the extent of Alamar Blue Reduction (mean±SEM) in the same experiments as in FIG. 1. Extent of reduction relates to metabolic activity of the cells during the 18 hours post-transfection.

FIG. 1 shows the CAT Expression (Mean±SEM) for Different treatments. Each experiment is performed in triplicate. FIG. 2 shows the extent of Alamar Blue Reduction (mean±SEM) in the same experiments as in FIG. 1. Extent of reduction relates to metabolic activity of the cells during the 18 hours post-transfection.

Discussion

The CAT minizyme contained the new linker 5'gtttt. When tested against a short 17-mer synthetic RNA substrate in vitro at 37° C., the minizyme cleaved the substrate with a reasonable rate constant (~0.5 min$^{-1}$, t½~1.4 minutes). In all experiments a constant number of cells (8×10$^4$) were seeded and treated identically with the exception of the added oligonucleotides. Based on observed CAT activity, the random 17-mer does not appear to be an appropriate control molecule. Accordingly tRNA was included in two of the experiments to provide an alternative control.

The minizyme and the DNA antisense show similar levels of suppression (52±9%, 54±9%, respectively) and both are significantly more effective than the inactivated minizyme (94± 25%, mean results Table 3). Thus both the minizyme and the antisense are showing activity in this cultured cell system.

We have been mindful of the danger of selecting a single protein or mRNA level as a specificity control and have therefore monitored the rate of general metabolism (by Alamar Blue reduction) as a measure of the specificity of the test molecules. It is interesting to note that the minizyme is apparently less toxic than the antisense in all experiments (Table 2, FIG. 2). Therefore the relative activity of the minizyme may be greater than that of the antisense, since a proportion of the apparent activity of the antisense molecule could result from a reduction in cell metabolism compared with minizyme treated cells.

Example 3

The Activities of DNA-armed Ribozymes and Minizymes against Interleukin-2 mRNA

Assays for Interleukin-2

Indirect assay. This assay is based on the ability of interleukin-2 (IL2) to promote the growth of the mouse T-cell line, CTLL-2. IL2 is absolutely required for the growth of CTLL-2 cells, and so the assay is specific for IL2.

Peripheral blood mononuclear cells (PBMN cells) are transfected with the test molecules using DOTAP for 6–8 hours. Following transfection, the PBMN cells are stimulated with PHA for about 16 hours in order to produce IL2. Interleukin-2 is secreted from these cells into the surrounding medium. Supernatant from the PBMN cells is added to CTLL-2 cells, and the CTLL-2 cells are allowed to grow overnight. The CTLL-2 cells are then pulsed with $^3$H-thymidine for about 4 hours, are harvested, and DNA-associated radioactivity is determined. Since IL2 promotes the growth of CTLL-2 cells, a high radioactive count (high level of incorporated $^3$H-thymidine) indicates high levels of IL2, and hence a test molecule with poor activity against IL2 in the PBMN cells.

The PBMN cells are from humans. For a particular experiment, the cells are from a single donor. For repeated experiments, the cells are from different donors. Thus, a factor in any variability in results from repeated experiments could be due to differing responses from patients.

Direct assay. Interleukin-2 has both endocrine and paracrine activities. Thus the IL2 produced by the T-cells promotes the growth of the same T-cells. In the direct assay, PBMN cells (which are rich in T-cells) are transfected with the test molecules for 12 hours, stimulated with PHA for about 48 hours, pulsed with $^3$H-thymidine, and then harvested approximately 18 hours later.

EASIA. Although the two assays described above are specific for interleukin-2, they do not detect IL2 bound to its soluble receptor. Thus, the indirect and direct assays are functional assays for IL2, rather than quantitative assays measuring absolute levels of IL2 mRNA or protein. To measure total amounts of IL2 contained in the supernatants from control and transfected cells, assays were done using IL2-EASIA (MADGENIX) in microtitre plates. This is a solid-phase Enzyme Amplified Sensitivity Immuno-Assay.

The Molecules Tested

The following molecules (2–7) have been synthesized and tested using one or more of the above assays. Molecule 4 is a minizyme with 5' d(GTTTT) linker which has been rendered inactive by replacing the conserved $A_{14}$ by a G. In the sequences below, ribonucleotides are denoted by uppercase letters and deoxyribonucleotides by lower-case letters. (Seq ID NO: 23–29)

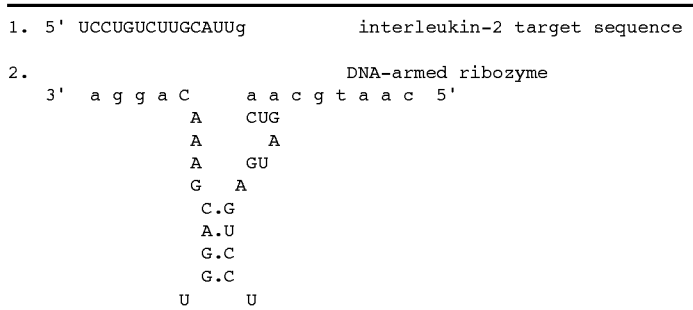

```
1.  5' UCCUGUCUUGCAUUg        interleukin-2 target sequence

2.                            DNA-armed ribozyme
       3'  a g g a C    a a c g t a a c  5'
                    A      CUG
                    A        A
                    A       GU
                    G   A
                    C.G
                    A.U
                    G.C
                    G.C
                  U     U
```

-continued

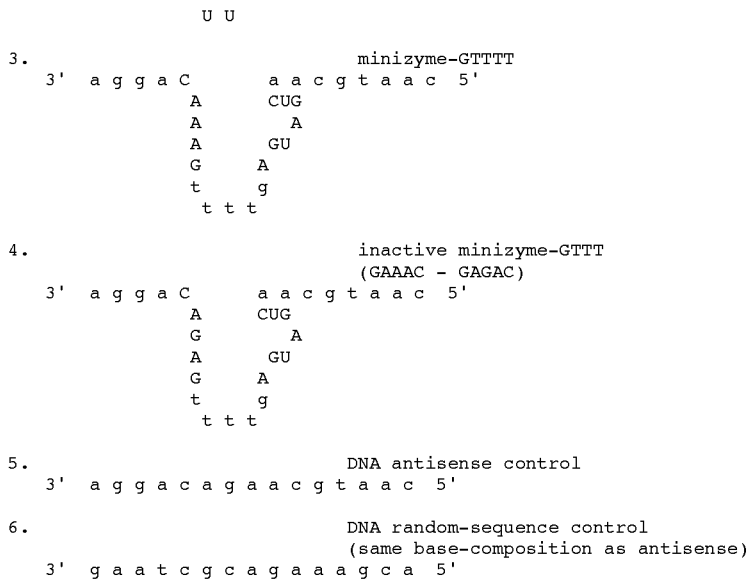

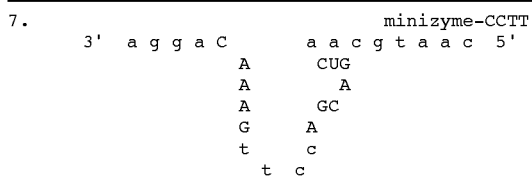

Activities of DNA-armed Ribozymes and Minizymes

Figure 3:
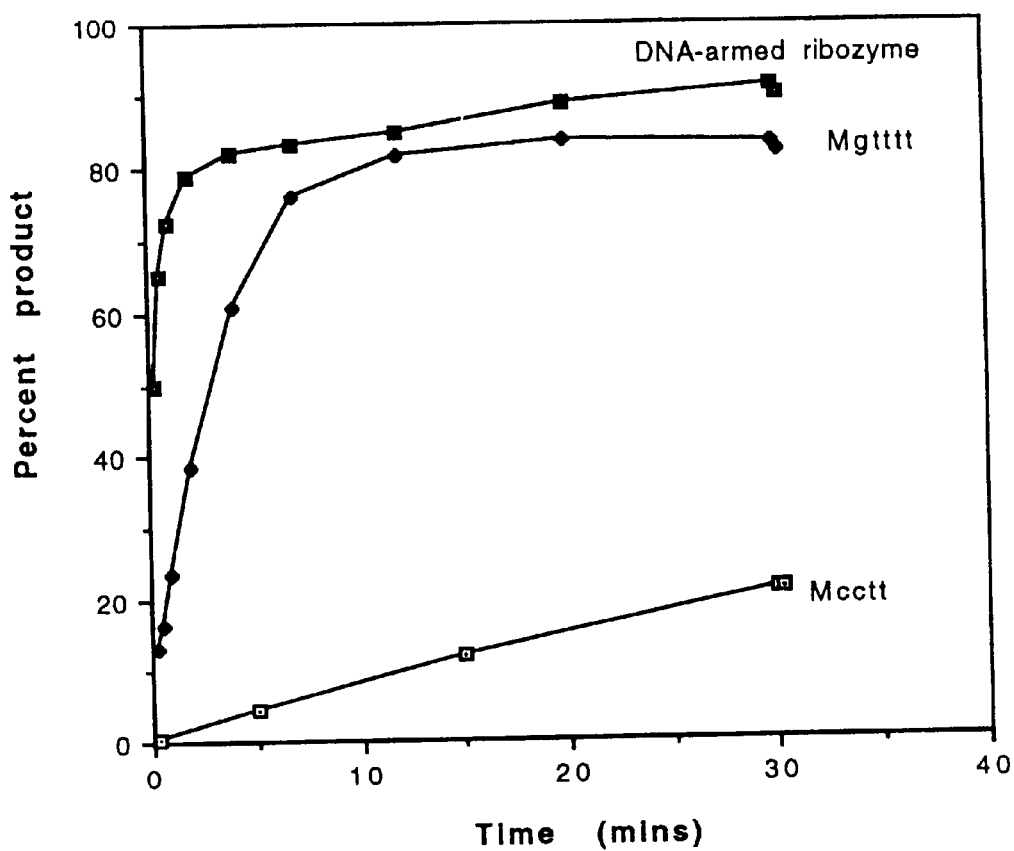
FIG. 3 shows the cleavage of the IL-2 substrate at 37° C. by minizymes (with cctt and gtttt linkers) and a ribozyme with DNA arms.

The original set of molecules synthesized for testing contained the DNA-armed ribozyme, the minizyme with d(CCTT) linker, the DNA antisense, and the DNA random-sequence control (molecules 2, 7, 5 and 6 respectively). In these first experiments using the indirect assay, with transfection concentrations of test molecules at 10 $\mu$M, the DNA-armed ribozyme showed good activity against IL2, while the minizyme with d(CCTT) linker and the DNA random-sequence control showed no significant activity; the DNA antisense showed about 50% the activity of the DNA-armed ribozyme. The activities of the DNA-armed ribozyme and the minizyme in cells correlated with the observed cleavage activities of these molecules as measured against a short synthetic IL2 substrate in vitro. Since the cleavage rate shown by the minizyme with d(CCTT) linker was extremely slow, we investigated the reason for this poor activity. In this investigation we found that, by changing the linker from 5' d(CCTT) to 5' d(GTTTT), the cleavage rate of the minizyme could be increased 30-fold. The cleavage activities of the DNA-armed ribozyme, the minizyme with d(CCTT) linker, and the new minizyme with d(GTTTT) linker, against their cognate, short substrate (molecule 1 above) at 37° C., are shown in FIG. 3.

Following the discovery of the highly-active minizyme with d(GTTTT) linker, we synthesized in large scale the DNA-armed ribozyme, the minizyme with d(GTTTT) linker, an inactivated minizyme with d(GTTTT) linker, the DNA antisense, and the DNA random-sequence control (molecules 2–6 above).

Results from Independent Experiments using Molecules 2–6

In the tables below, results are presented for individual experiments (each done in duplicate or triplicate). In the first of each pair of tables, the data show the effectiveness of the test molecules against IL2, relative to that of the DNA random-sequence control taken as having 0% inhibitory effect. Since ribozymes and minizymes are being developed as alternatives to other oligonucleotide-based therapies, we believe that the inhibitory effects of these molecules, over and above the non-specific effects of a randomly-chosen oligonucleotide, are the data of interest. In most experiments, tRNA was also included as an additional control molecule. Generally, the DNA random-sequence control showed some activity against IL2 relative to tRNA, and so these data are presented for information (relative to tRNA taken as having 0% inhibitory effect) in the second of each pair of tables.

Indirect assay. % Inhibition of IL2 as Measured in Individual Experiments by the Indirect Assay. (Table 4)

TABLE 4A

Data relative to DNA random-sequence control.

| | Transfection concentration | | | | | |
|---|---|---|---|---|---|---|
| Test molecule | 5 $\mu$M | | 10 $\mu$M | | 20 $\mu$M | |
| DNA-armed Rz | 33 | 36 | 56 | 33 | 68 | 70 |
| Minizyme-GTTTT | 31 | 41 | 45 | 38 | 45 | 60 |
| Mz-inactive | 5 | 5 | 34 | −20 | 24 | 32 |
| DNA antisense | 10 | 30 | 34 | 0 | 9 | 17 |

TABLE 4B

Data relative to tRNA.

| | Transfection concentration | | | | | |
|---|---|---|---|---|---|---|
| Test molecule | 5 $\mu$M | | 10 $\mu$M | | 20 $\mu$M | |
| DNA-armed Rz | 45 | 44 | 61 | 49 | 77 | 82 | — |
| Minizyme-GTTTT | 43 | 48 | 51 | 53 | 60 | 76 | 83 |

TABLE 4B-continued

Data relative to tRNA.

| Test molecule | Transfection concentration | | | | | | |
|---|---|---|---|---|---|---|---|
| | 5 μM | | 10 μM | | | 20 μM | |
| Mz-inactive | 22 | 16 | 41 | 9 | 45 | 60 | 37 |
| DNA antisense | 25 | 39 | 41 | 24 | 34 | 51 | 63 |
| DNA random control | 18 | 12 | 11 | 24 | 28 | 41 | — |

Direct Assay. % Inhibition of IL2 as Measured in Individual Experiments by the Direct Assay. (Table 5)

TABLE 5A

Data relative to DNA random-sequence control.

| Test molecule | Transfection concentration 10 μM | |
|---|---|---|
| DNA-armed Rz | 65 | 69 |
| Minizyme-GTTTT | 41 | 50 |
| Mz-inactive | 25 | 22 |
| DNA antisense | 18 | 38 |

TABLE 5B

Data relative to tRNA.

| Test molecule | Transfection concentration 10 μM | |
|---|---|---|
| DNA-armed RZ | 70 | 75 |
| Minizyme-GTTTT | 50 | 60 |
| Mz-inactive | 36 | 38 |
| DNA antisense | 30 | 50 |
| DNA random control | 15 | 20 |

TABLE 6

EASIA
Transfection concentration 20 μM.

| Test molecule | IU/ml | % inhibition relative to tRNA |
|---|---|---|
| Minizyme-GTTTT | 70 | 72% |
| Mz-inactive | 120 | 52% |
| control (tRNA) | 250 | — |

% Inhibition Averaged over Five Experiments at 10 μM Transfection Concentration (Results are averaged from data given above, from three experiments using the indirect assay and two experiments using the direct assay).

TABLE 7

| Test molecule | % inhibition (standard deviation) relative to DNA random control | % inhibition (standard deviation) relative to tRNA |
|---|---|---|
| DNA-armed Rz | 52 (15) | 60 (12) |
| Minizyme-GTTTT | 43 (4) | 52 (4) |
| Mz-inactive | 13 (19) | 28 (13) |
| DNA antisense | 24 (14) | 37 (9) |
| DNA random control | — | 16 (5) |

Toxicity to Cells

Cell viability was tested using acridine orange; dead cells appear orange and living cells appear green in the presence of this indicator. The assays were done on PBMN cells that were transfected with the test molecules for a period of 26–30 hours, but were not stimulated with PHA.

For transfection concentrations of test molecules at 5, 10 or 20 μM, approximately 4–8% of the cells were dead. These values were similar for control cells. Therefore, for incubation periods of 26–30 hours, the test molecules showed no significant toxicity to the cells.

Summary of Results

The DNA-armed ribozyme and the minizyme, with d (GTTTT) linker, show activity specifically against interleukin-2 in human PBMN cells. The effects of these two molecules are greater than those measured for a DNA antisense molecule and an inactivated minizyme directed to the same target site on the IL2 mRNA, at transfection concentrations of 5, 10 and 20 μM. The molecules do not appear to be toxic to cells over a 30-hour period.

Sequences of Mini-ribozymes and Ribozymes

Upper-case letters represent ribonucleotides, lower-case letters represent deoxyribonucleotides.

Interleukin-2 system (Seq. ID No. 30–35)

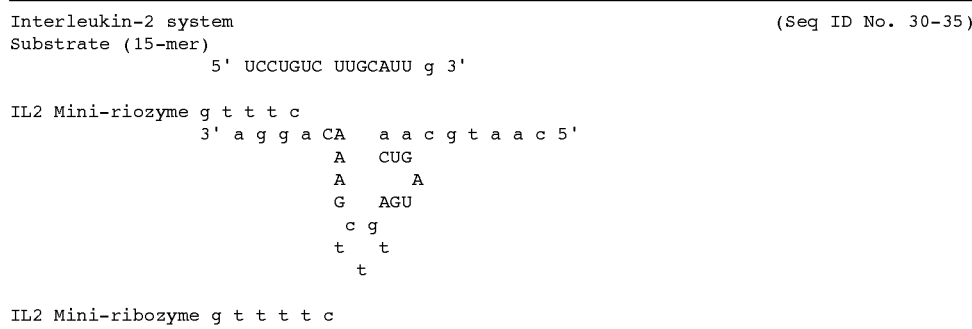

```
Interleukin-2 system                                      (Seq ID No. 30-35)
Substrate (15-mer)
                  5' UCCUGUC UUGCAUU g 3'

IL2 Mini-riozyme g t t t c
                3' a g g a CA    a a c g t a a c 5'
                           A     CUG
                           A       A
                           G     AGU
                             c g
                             t   t
                                t IL2 Mini-ribozyme g t t t t c
```

Experimental Data

The method for determining rates of cleavage ($k_{obs}$) of short substrates by the miniribozymes is as described in Experiment 1. Initial experiments at pH 8.2 showed the reactions for these TAT and IL2 mini-ribozymes and the RC ribozyme are very fast, with the reactions being completed in less than 1 minute. Therefore the reactions were also performed at a lower pH (pH 7.13) where the reactions are slower; these data show more clearly the relative activities of the various molecules.

TABLE 8(a)

Data from independent experiments at 37° C., 10 mM MgCl₂, pH 8.2

| System | gtttc mini-ribozyme $k_{obs}$ (min⁻¹) | % P∞ | gttttc mini-ribozyme $k_{obs}$ (min⁻¹) | % P∞ | "RC" ribozyme $k_{obs}$ (min⁻¹) | % P∞ | gtttt minizyme $k_{obs}$ (min⁻¹) | % P∞ |
|---|---|---|---|---|---|---|---|---|
| TAT | 1.372* | 89.8 | — | | 2.993* | 92.9 | 0.179 | 89.7 |
|  | 1.938* | 82.5 |  |  | 1.866 | 93.8 | 0.190 | 90.8 |
| IL2 | 2.41* | 74.3 | 2.40 | 84.6 | 1.29 | 81.7 | 0.299 | 83.5 |
|  |  |  |  |  |  |  | 0.287 | 85.3 |
|  |  |  |  |  |  |  | 0.225 | 84.9 |

TABLE 8(b)

Data from independent experiments at 37° C., 10 mM MgCl₂, pH 7.13

| System | gtttc mini-ribozyme $k_{obs}$ (min⁻¹) | % P∞ | gttttc mini-ribozyme $k_{obs}$ (min⁻¹) | % P∞ | "RC" ribozyme $k_{obs}$ (min⁻¹) | % P∞ | gtttt minizyme $k_{obs}$ (min⁻¹) | % P∞ |
|---|---|---|---|---|---|---|---|---|
| TAT | 0.099 | 85 | — |  | 0.372 | 90 | 0.012 | 100 |
| IL2ᵃ | 0.116 | 88 | 0.198 | 82 | 0.049 | 98 | 0.018 | 100 |
| IL2ᵇ | 0.121 | 82 |  |  | 0.039 | 88 |  |  |
| IL2ᶜ |  |  | 0.177 | 82 | 0.062 | 84 | 0.021 | 83 |

*This reaction proceeds in two steps, with an initial fast reaction followed by a slower reaction; $k_{obs}$ for the initial fast reaction is given.
IL2ᵃ - 15-mer IL2 substrate, IL2 (gtttc) mini-ribozyme, IL2 "RC" Ribozyme (DNA arms + stem), and IL2 (gtttt) minizyme are from the first set of syntheses.
IL2ᵇ - 15-mer IL2 substrate, IL2 (gtttc) mini-ribozyme, and IL2 "RC" Ribozyme (DNA arms + stem) are from a second set of syntheses.
IL2ᶜ - 15-mer IL2 substrate is from second synthesis, and IL2 (gttttc) mini-ribozyme, IL2 "RC" Ribozyme (DNA arms + stem) and IL2 (gtttt) minizyme are from first syntheses. Table 9(a) Averaged data from experiments at 37° C., 10 mM MgCl₂, pH 8.2 (Where there are no standard deviations given in parentheses, the experiment was done only once.)

| System | gtttc mini-ribozyme $k_{obs}$ (min⁻¹) | % P∞ | gttttc mini-ribozyme $k_{obs}$ (min⁻¹) | % P∞ | "RC" ribozyme $k_{obs}$ (min⁻¹) | % P∞ | gtttt minizyme $k_{obs}$ (min⁻¹) | % P∞ |
|---|---|---|---|---|---|---|---|---|
| TAT | 1.7* | 86 | — |  | 2.4* | 93 | 0.185 | 90 |
|  | (0.4) | (5) |  |  | (0.8) | (1) | (0.008) | (1) |
| IL2 | 2.4* | 74 | 2.40 | 85 | 1.3 | 82 | 0.27 | 85 |
|  |  |  |  |  |  |  | (0.04) | (1) |

TABLE 9(b)

Averaged data from experiments at 37° C., 10 mM MgCl₂, pH 7.13

| System | gtttc mini-ribozyme $k_{obs}$ (min⁻¹) | % P∞ | gttttc mini-ribozyme $k_{obs}$ (min⁻¹) | % P∞ | "RC" ribozyme $k_{obs}$ (min⁻¹) | % P∞ | gtttt minizyme $k_{obs}$ (min⁻¹) | % P∞ |
|---|---|---|---|---|---|---|---|---|
| TAT | 0.099 | 85 | — |  | 0.372 | 90 | 0.012 | 100 |
| IL2 | 0.119 | 85 | 0.19 | 82 | 0.050 | 90 | 0.020 | 92 |
|  | (.004) | (4) | (.01) |  | (.011) | (7) | (.002) | (12) |

Comments in ribozyme publications teach that helix II can be reduced to 2 b.p. without loss of activity, but further reduction to 1 b.p. results in at least a 10-fold reduction in activity—see data from Tuschl & Eckstein (1993) and from Long and Uhlenbeck (1994). Note that these data are for all-RNA ribozymes; nobody has published similar data for DNA-containing ribozymes with just one b.p. in helix II.

The faster cleavage rates (see Tables 9 and 10) shown by the IL2 gtttc and gttttc mini-ribozymes, compared with that for the IL2 "RC" full-sized ribozyme, were totally unexpected, considering results reported in the papers referred to above. To check whether or not these unexpected results were due to an error in synthesis or processing of the IL2 molecules (in particular the IL2 "RC" ribozyme), we synthesized a second batch of IL2 "RC" ribozyme, IL2 gtttc mini-ribozyme, and the IL2 15-mer substrate, and checked rates of cleavage. As shown by the data in Table 8 (b), similar cleavage rates were observed for the IL2 molecules from two independent syntheses. These data have been averaged and are presented in Table 10 as cleavage rates for mini-ribozymes gtttc and gttttc relative to full-sized ribozymes RC, and also relative to the minizyme gtttt.

TABLE 10

Relative $k_{obs}$ at pH 7.13

| System | gtttc/"RC" Rz | gttttc/"RC" Rz | gtttc/gtttt | gttttc/gtttt |
|---|---|---|---|---|
| TAT | 0.27 | — | 8.3 | — |
| IL2 | 2.4 | 3.8 | 6.0 | 9.5 |

The gtttc mini-ribozymes have a 3-fold reduction (TAT) or a 2.4-fold improvement (IL2) compared with their respective ribozymes "RC" (Table 10).

All-RNA mini-ribozymes

In the above tables, we have compared the cleavage activities of gtttc and gttttc mini-ribozymes with those of "RC" ribozymes, since they have similar patterns of deoxyribonucleotides and ribonucleotides in their compositions. Here, we present data for an all-RNA mini-ribozyme, and compare its cleavage activity with that of an all-RNA ribozyme, as the appropriate control. The GUUUUC mini-ribozyme cleaves with a rate about 5-fold slower at pH 7.13 than the analogous all-RNA ribozyme.

TABLE 11

Averaged data from experiments at 37° C., 10 mM MgCl₂, pH 7.13

| | GUUUUC mini-ribozyme | | "RA" ribozyme | |
|---|---|---|---|---|
| System | $k_{obs}$ | % P∞ | $k_{obs}$ | % P∞ |
| IL2 | 0.318(.001) | 74(2) | 1.50*(.02) | 66(2) |

*This reaction proceeds in two steps, with an initial fast reaction followed by a slower reaction; $k_{obs}$ for the initial fast reaction is given.

Comments on Expected Activity in Cells

We know that the IL2 minizyme with gtttt linker, which has $k_{obs}$=0.27 min⁻¹ (at pH 8.2), is active in cells. Therefore, the IL2 mini-ribozymes with gtttc and gttttc linkers, which have $k_{obs}$>1 min⁻¹ at pH 8.2, and which target the same site in the IL2 mRNA, are also likely to be active in cells, and possibly will be more effective molecules in cells than the gtttt minizyme. For similar reasons, the all-RNA IL2 mini-ribozyme, which has $k_{obs}$=0.3 min⁻¹ at pH 7.13 (and, by extrapolation, $k_{obs}$=3 min⁻¹ at pH 8.2) should not be limited by its rate of cleavage in cells.

References

Altman, S. (1987) *Adv. Enzymol.* 62:1.
Baer, M. F., et al. (1990) *Methods Enzymol.* 181:569.

Been, M. D., and Cech, T. R. (1988) *Science* 239:1412
Boehm, S., (1987) *FEBS Letters*, 220: 283–287.
Breaker, R. R. and Joyce, G. F. (1994) TIBTECH 12:268–275.
Bruening, G., (1987) Methods in Enzymology, 180:546–558.
Bruening, G. (1990) *Seminars in Virol.* 1:127.
Bryant, J. (1992) Tibtech 10:342–343.
Buzayan et al., (1986), Proc. Natl. Acad. Sci. USA 83:8859–8862.
Cameron et al., (1989), Proc. Natl. Acad. Sci., 86:9139–9143.
Cantor, G. H., et al. (1993) *Proc. Natl. Acad. Sci. U.S.A.* 90:10932–10936.
Carruthers et al. (1987), Methods in Enzymology, 154: 287–313).
Castanotto, D., et al. (1992) *Critical Rev. in Eukaryotic gene Exp.* 2:331–337.
Cech, T. R., (1987) Science, 236: 1532–1539.
Cech, T. R., et al. (1981) *Cell* 27:487.
Chuat, J. et al., (1989) Biochemical and Biophysical Research Communications, 162: 1025–1029.
Cotten, M., (1990) Tibtech 8: 174–178.
Cotten, M. et al., (1989) The EMBO Journal, 8: 3861–3866.
Dahm, S. C., et al., (1990) Biochimie 72:819–823.
Dropulic, B., et al. (1992) *J. Virol.* 66:1432–1441.
Eckner, R. et al., (1991) The EMBO Journal, 10: 3513–3522.
Epstein, L. M., and Gall, J. G., (1987) *Cell* 48:535.
Epstein, L. M., and Gall, J. G., (1989) *Cold Spring Harbour Symp. Quant. Biol.* 52:261.
Evans, G. J., et al. (1992) *Biochem. Soc. Trans.* 20:344S.
Foehler et al. (Nucleic Acids Research (1986) 14: 5399–407).
Forster et al., (July 1987), Cell, 50:9–16.
Forster, A. C. et al., (1988) Nature, 334:265–267.
Forster, A. C. and Symons, R. H., (1987) Cell, 49: 211–220.
Friedman, T., (1989) Science 244: 1275–1280.
Gallie, D. R., et al. (1991) *Mol. Gen. Genet.* 228:258–264.
Goodchild, J., et al. (1991) Archives to Biochem & Biophys. 284:386–391.
Green, R., and Szostak, J. W. (1992) *Science* 258:1910.
Goodchild, J. et al., (1990) Poster No. 12 at Conf in San Diego.
Hanahan et al., (1983), J. Mol. Biol 166).
Haseloff, J. and W. L. Gerlach, (1988) Nature, 334:585–591.
Haseloff et al., (1989), Gene, 82:43–52.
Hendry, P., McCall, M. J., Santiago, F. S., & Jennings, P. A. *Nucl. Acids. Res.*, 20, 5737–5741 (1992).
Herschlag, D., and Cech, T. R. (1990) *Nature* 344:405.
Hogan, B. et al., (1986) Manipulating the Mouse Embryo, A Laboratory Manual, Cold Spring Harbor.
Hogan, B. et al., (1989), Science, 244: 1275.
Homann, M., et al. (1993) *Nucleic Acid Res.* 28:2809–2814.
Howard, E. A., et al. (1987) *Planta* 170:535–540.
Huillier, A. et al., Ribozyme Mediated Suppression of Lactalbumin Expressed in C1271 Cells by T7/Vaccinia Virus, (Abstract from conference proceedings).
Hutchins, C. J. et al., (1986) Nucleic Acids Research, 14:3627–3635.
Jefferies, A. C., et al., (1989) Nucl. Acids Res. 17:1371–1377.
Joyce, G. F. (1992) *Sci. Am.* 267:90.
Karnail, U. and Wasternack, C. (1992) *J. Biochem.* 24:493–497.
Kikuchi, Y. et al., (1991) Nucleic Acids Research, 19:6751–6755.
Kinsey, P. T. and Sandmeyer, S. S. (1991) *Nucleic Acid Res.* 19:1317–1324.
Koizumi et al., (1988) FEBS Letters, 228:228–230.
Koizumi et al., (1989) Nucleic Acids Research, 17:7059–7071.
Kruger, K., et al. (1982) *Cell* 31:147.
Kunkel, T. A., et al. (1987) *Methods in Enzymology* 154:367–382.
Lamb, J. W. & Hay, R. T., (1990) J. Gen. Virol., 71:2257–2264.
L'Huillier, P. J. L., et al. (1992) *EMBO* 11:4411–4418.
Llewellyn et al., (1987), J. Mol. Biol., 195: 115–123.
Maliga, P. (1993) Tibtech 11:101–106.
Mazzolini, L., et al. (1992) *Plant Molecular Biology* 20:715–731.
McClain et al., (1987) Science 238:527–530.
Miller, W. A. et al., (1991) Virology, 183:711–720.
Nichols, M., et al. (1988) *Proc. Natl. Acad. Sci. U.S.A.* 85:1379.
Noller, H. F., et al. (1992) *Science* 256:1416.
Pace, N. R., and Smith, D., (1990) *J. Biol. Chem.* 265:3587.
Pan, T., and Uhlenbeck, O. C. (1992) *Nature* 358:560.
Perriman et al., (1992), Gene, 113:157.
Perriman, R., et al. (1993) *Antisense Res. & Dev.* 3:253–263.
Perreault et al., (1990), Nature, 344:565–567.
Perreault, J. P., et al., (1991) Biochem. 30:4020–4025.
Piccirilli, J. A., et al. (1992) *Science* 256:1420.
Prody et al., (1986), Science 231: 1577–1580.
Pyle, A. M. (1993) *Science* 261:709–714.
Robertson, D. L., and Joyce, G. F. (1990) *Nature* 344:467.
Ruffner, D. E. et al., (1990) Biochemistry, 29: 10695–10702.
Ruffner, D. E. et al., (1989) Gene, 82:31–41.
Sambrook, J. et al., (1989), Molecular Cloning, A Laboratory Manual, 2nd Edition, Cold Spring Harbor Press.
Sampson, et al., (1987) Cold Spring Harbor Sym Quant. Biol. 52:267–275.
Saenger, W. (1984), Principles of Nucleic Acid Structure, Springer-Verlag, N.Y.
Sarver, N. et al., (1990) Science, 247:1222–1224.
Saville, B. J. and Collins, R. A. (1990) *Cell* 61:685.
Saxena, S. et al., (1990) J. Biol. Chem., 265:17106–17109.
Scanlon, K. et al., (1991) Proc. Natl. Acad. Sci. USA, 88:10591–10595.
Sheldon, C. C. & Symons, R. H., (1989), Nucleic Acids Research, 17:5679–5686.
Sheldon, C. C. & Symons, R. H., (1989) Nucleic Acids Research, 17:5665–5678.
Shimamoto, K., Terada, R., Izawa, T., and Fujimoto, H. (1989) Nature 338:274–276.
Sioud, M. and Drlica, K. (1991) *Proc. Natl. Acad. Sci. U.S.A.* 88:7303–7307.
Sioud, M., et al. (1992) *J. Mol. Biol.* 223:831–835.
Sleigh, M. J. *Anal. Biochem.* 156, 251–256 (1986)
Strobel, S. A. et al., (1991), Nature 350: 172–174 and references therein.
Sober, H. (1970), CRC Handbook of Biochemistry, Second edition.
Sproat et al. (Oligonucleotide Synthesis—A Practical Approach, IRL Press, Oxford (1984) M. J. Gait—Editor, pp. 83–115).
Sullenger, B. A. and Cech, T. R. (1993) *Science* 262:1566–1569.
Stange, N. and Beier, D. (1986) *Nucleic Acid Res.* 14:8961.
Steinecke, P., et al. (1992) *EMBO* 11:1525–1530.
Symons, R. H., (1989) TIBS, 14:445–450.
Symons, R. H., (1990) *Seminars in Virol.* 1:117.
Szostak, J. W. (1992) TIBS 17:89–93.

Tabler, M. & Tsagris, M., (1991) Gene, 108:175–183.
Taylor, J., (1990) *Seminars in Virol.* 1:135.
Uhlenbeck et al., (1987), Nature, 328:596–600.
Uhlmann et al., (1990), Chem. Revs., 90:544–584.
Waugh, D. S., et al. (1989) *Science* 244:1569.
Yang, et al., (1990) Biochemistry 29:11156–11160.

Zaug, A. J. et al, (1984), Science, 224:574–578.
Zaug, A. J. & Cech, T. R., (1986a) Science, 231:473–474.
Zaug, A. J. et al., (1986b) Nature, 324:429–433.
Zaug, A. J., and Cech, T. R. (1986) *Biochemistry* 25:4478.
Zhao, J. J. and Pick, L. (1993) *Nature* 365:448–451.

---

What is claimed is:

1. A compound having the formula:

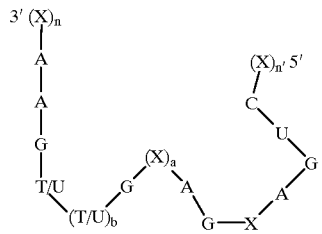

wherein each X represents a nucleotide which may be the same or different and may be substituted or modified in its sugar, base or phosphate;

wherein $(T/U)$-$(T/U)_b$-G represents T-$(T)_b$-G or U-$(U)_b$-G, with the proviso that b represents an integer which is 3 or 4;

wherein each of $(X)_n$ and $(X)_{n'}$ represents an oligonucleotide having a predetermined sequence which is capable of hybridizing with an RNA target sequence;

wherein each of n and n' represents an integer which defines the number of nucleotides in the oligonucleotide;

wherein each solid line represents a covalent bond between the nucleotides located on either side thereof; and wherein a represents an integer which defines a number of nucleotides with the proviso that a may be 0 or 1 and if 0, the A located 5' of $(X)_a$ is bonded to the G located 3' of $(X)_a$.

2. The compound of claim 1, wherein the oligonucleotide 3'-$(X)_n$- is 3'-$(X)_{n-1}$-A-.

3. The compound of claim 1, wherein the oligonucleotide 3'-$(X)_n$- is 3'-$(X)_{n-2}$-C-A-.

4. The compound of claim 1, wherein $(X)_a$ is absent.

5. The compound of claim 1, wherein the integer b of $(T/U)_b$ is equal to 3.

6. The compound of claim 1, wherein the integer b of $(T/U)_b$ is equal to 4.

7. The compound of claim 1, wherein each X is a deoxyribonucleotide.

8. The compound of claim 1, wherein each X is a ribonucleotide.

9. The compound of claim 1, wherein $(T/U)_b$ is a $(T)_b$.

10. A compound having the formula:

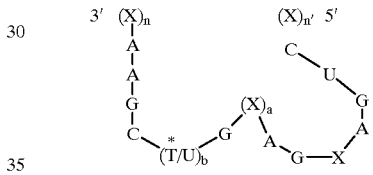

wherein each X represents a nucleotide which may be the same or different and may be substituted or modified in its sugar, base or phosphate;

wherein C-$(T/U)_b$-G represents C-$(T)_b$-G or C-$(U)_b$-G, with the proviso that b represents an integer which is 3 or 4;

wherein each of $(X)_n$ and $(X)_{n'}$ represents an oligonucleotide having a predetermined sequence which is capable of hybridizing with an RNA target sequence;

wherein each of n and n' represents an integer which defines the number of nucleotides in the oligonucleotide;

wherein * represents a base pair between the nucleotides located on either side thereof;

wherein each solid line represents a covalent bond between the nucleotides located on either side thereof; and wherein a represents an integer which defines a number of nucleotides with the proviso that a may be 0 or 1 and if 0, the A located 5' of $(X)_a$ is bonded to the G located 3' of $(X)_a$.

11. The compound of claim 10, wherein the oligonucleotide 3'-$(X)_n$- is 3'-$(X)_{n-1}$-A-.

12. The compound of claim 10, wherein the oligonucleotide 3'-$(X)_n$- is 3'-$(X)_{n-2}$-C-A-.

13. The compound of claim 10, wherein $(X)_a$ is absent.

14. The compound of claim 10, wherein the integer b of $(T/U)_b$ is equal to 3.

15. The compound of claim 10, wherein the integer b of $(T/U)_b$ is equal to 4.

16. The compound of claim 10, wherein each X is a deoxyribonucleotide.

17. The compound of claim 10, wherein each X is a ribonucleotide.

18. The compound of claim 10, wherein $(T/U)_b$ is a $(T)_b$.

19. A composition which comprises a compound of claim 1 in association with an acceptable carrier.

20. A composition which comprises a compound of claim 10 in association with an acceptable carrier.

21. A transfer vector containing a deoxyribonucleotide sequence which on transcription gives rise to the compound of claim 1 or claim 10.

22. The transfer vector of claim 21, wherein the transfer vector is a bacterial plasmid, a bacteriophage DNA, a cosmid, or an eukaryotic viral DNA.

23. The transfer vector of claim 21, wherein the oligonucleotide transfer vector is a plant DNA virus, a geminivirus or an infective phage particle.

24. The transfer vector of claim 21, wherein the oligonucleotide transfer vector is packaged and contains the promoter sequences for RNA polymerase II or RNA polymerase III.

25. A host cell transformed by the transfer vector of claim 21.

26. The host cell of claim 23, wherein the host cell is a prokaryotic host cell or an eukaryotic host cell.

27. The prokaryotic host cell of claim 24, wherein the prokaryotic host cell is an *E. coli* host cell.

28. The eukaryotic host cell of claim 24, wherein the eukaryotic host cell is a monkey COS host cell, a Chinese hamster ovary host cell, a mammalian host cell or a plant host cell.

29. A method of cleaving a target mRNA which comprises administering an effective amount of the compound of claim 1 or 10.

30. A method of cleaving a target mRNA in a host cell which comprises administering to the host cell an effective amount of the compound of claim 1 or 10 or the transfer vector of claim 21.

31. The compound of claim 1 or 10 which further comprises an antisense nucleic acid which is capable of hybridizing with an RNA target sequence.

32. The compound of claim 1 or 10 which further comprises at least one additional non-naturally occurring oligonucleotide compound which comprises nucleotides whose sequence defines a conserved catalytic region and nucleotides whose sequence is capable of hybridizing with a predetermined target sequence.

33. The compound of claim 32 wherein the additional non-naturally occurring oligonucleotide compound is a hammerhead ribozyme, a minizyme, an RNAase P ribozyme or a combination thereof.

* * * * *

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

NCUGANGANG UUGAAN                            16

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:2:

NCUGANGANG UCGAAN                            16

(2) INFORMATION FOR SEQ ID NO:3:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:3:

NNNNNNNCUG AUGAGTTTTG AAACNNNNN            29

(2) INFORMATION FOR SEQ ID NO:4:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:4:

UCCUGUCUUG CAUUG                              15

(2) INFORMATION FOR SEQ ID NO:5:

(i) SEQUENCE CHARACTERISTICS:
      (A) LENGTH: 29 base pairs

```
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CAATGCAACU GAUGAGTTTT GAAACAGGA                                               29

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

CAATGCAACU GAUGAGTTTT GAAACAGGA                                               29

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CAATGCAACU GACGACCTTG AAACAGGA                                                28

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

CAATGCAACU GAUGANGAAA CAGGA                                                   25

(2) INFORMATION FOR SEQ ID NO:9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GGAAGUCAGC CUA                                                                13

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
```

(xi) SEQUENCE DESCRIPTION: SEQ ID NO:10:

GTCCTAGGCT CUGAUGAGTT TTGAAACTTC CTGGA        35

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GTCCTAGGCT CUGAUGATTT TGAAACTTCC TGGA        34

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

UUCCAUGUCG GCAGAAT        17

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

ATTCTGCCCU GAUGAGTTTT GAAACATGGA A        31

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

ATTCTGCCCU GAUGATTTTG AAACATGGAA        30

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

ATTCTGCCCU GAUGAGGTTT GAAACATGGA A        31

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CCAGGCAGUC AGAUCAUCUT                                20

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

AAGATGATCT CUGAUGAGTT TTGAAACTGC CTGG                  34

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

AAGATGATCT CUGAUGATTT TGAAACTGCC TGG                   33

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

NNNNNNNNNN NNNNNNN                                   17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

ATTCTGCCGA CATGGAA                                   17

(2) INFORMATION FOR SEQ ID NO:21:

(i) SEQUENCE CHARACTERISTICS:
        (A) LENGTH: 31 base pairs (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:21:

ATTCTGCCCU GAUGAGTTTT GAAACATGGA A                                31

(2) INFORMATION FOR SEQ ID NO:22:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:22:

ATTCTGCCCU GAUGAGTTTT GAGACATGGA A                                31

(2) INFORMATION FOR SEQ ID NO:23:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:23:

UCCUGUCUUG CAUUG                                                  15

(2) INFORMATION FOR SEQ ID NO:24:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:24:

CAATGCAACU GAUGAGUCCU UUUGGACGAA ACAGGA                           36

(2) INFORMATION FOR SEQ ID NO:25:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:25:

CAATGCAACU GAUGAGTTTT GAAACAGGA                                   29

(2) INFORMATION FOR SEQ ID NO:26:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:26:

CAATGCAACU GAUGAGUUUU GAGACAGGA 29

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CAATGCAAGA CAGGA 15

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

ACGAAAGACG CTAAG 15

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

CAATGCAACU GACGACCUUG AAACAGGA 28

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

UCCUGUCUUG CAUUG 15

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

CAATGCAACU GAUGAGUUUC GAAACAGGA 29

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

CAATGCAACU GAUGAGTTTT CGAAACAGGA                              30

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

CAATGCAACU GAUGAGTCCT TTTGGACGAA ACAGGA                     36

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

CAAUGCAACU GAUGAGUUUU CGAAACAGGA                              30

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

CAAUGCAACU GAUGAGUCCU UUUGGACGAA ACAGGA                     36

(2) INFORMATION FOR SEQ ID NO:36:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:36:

GGAAGUCAGC CUA                                                13

(2) INFORMATION FOR SEQ ID NO:37:

(i) SEQUENCE CHARACTERISTICS:
        (A) LENGTH: 36 base pairs

-continued

```
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:37:

GTCCTAGGCT CUGAUGAGTT TTCGAAACTT CCTGGA                              36

(2) INFORMATION FOR SEQ ID NO:38:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:38:

GTCCTAGGCT CUGAUGAGTC CTTTTGGACG AAACTTCCTG GA                       42
```